United States Patent
Koizumi et al.

(10) Patent No.: US 6,762,205 B1
(45) Date of Patent: Jul. 13, 2004

(54) PHENYL SULFAMATE DERIVATIVES

(75) Inventors: Naoyuki Koizumi, Sagamihara (JP); Makoto Okada, Inagi (JP); Shigeki Iwashita, Kawasaki (JP); Shigehiro Takegawa, Kawasaki (JP); Takayoshi Nakagawa, Fujisawa (JP); Hiroo Takahashi, Sagamihara (JP); Tomohito Fujii, Kawasaki (JP)

(73) Assignee: Teikoku Hormone Mfg. Co., Ltd., Tokyo (JP)

( * ) Notice: Subject to any disclaimer, the term of this patent is extended or adjusted under 35 U.S.C. 154(b) by 72 days.

(21) Appl. No.: 10/019,693

(22) PCT Filed: Jul. 4, 2000

(86) PCT No.: PCT/JP00/04427

§ 371 (c)(1),
(2), (4) Date: Jan. 3, 2002

(87) PCT Pub. No.: WO01/02349

PCT Pub. Date: Jan. 11, 2001

(30) Foreign Application Priority Data

Jul. 6, 1999 (JP) .......................................... 11/191632

(51) Int. Cl.$^7$ ........................ A61K 31/18; C07C 309/00
(52) U.S. Cl. ..................... 514/602; 514/601; 514/608; 514/520; 514/524; 562/37; 562/45
(58) Field of Search ................................ 514/601, 602, 514/608, 518, 520, 524; 562/37, 45

(56) References Cited

U.S. PATENT DOCUMENTS

| | | | | |
|---|---|---|---|---|
| 3,082,238 A | * | 3/1963 | Dunbar et al. | 260/456 |
| 5,025,031 A | * | 6/1991 | Lo et al. | 514/602 |
| 5,192,785 A | * | 3/1993 | Lo et al. | 514/602 |

FOREIGN PATENT DOCUMENTS

| | | | |
|---|---|---|---|
| EP | 403185 | * | 12/1990 |
| JP | 1136687 | * | 9/1962 |
| JP | 56-83467 | | 7/1981 |
| JP | 56083467 | * | 7/1981 |
| WO | 97/32872 | | 9/1997 |

OTHER PUBLICATIONS

Chemical Abstract DN 59:21587, also cited as DE 1136687.*
Chemical Abstract DN 59:21586, also cited as U.S.P. 3082238.*
Chemical Abstract DN 95:186905, also cited as JP 56083467.*
Chemical abstract DN 119:249709, also cited as USP5192785.*
Chemica Abstract DN115:255820, also cited as 5025031.*
Chemical Abstract DN 116:20788, also cited as EP 403185.*
A. Purohit et al., "Recent Advances in the Development of Steroid Sulfatase Inhibitors", J. Steroid Biochem. Mol. Biol., 1999, vol. 69, No. 1–6, pp. 227–238.
Aparna Kolli et al., "Development of(p–O–sulfamoyl)–N–alkanoyl–phenylalkyl amines as non–steroidal estrone sulfatase inhibitors", J. Steroid Biochem. Mol. Biol., 1999, vol. 68, No. 1–2, pp. 31–40.
Guo–Hua Chu et al., "Synthesis and sulfatase inhibitory activities of (E)– and (Z)–4–hydroxytamoxifen sulfamates", Bioorg. Med. Chem. Lett., 1999, vol. 9, No. 2, pp. 141–144.

* cited by examiner

Primary Examiner—Richard L. Raymond
Assistant Examiner—Sudhaker B. Patel
(74) Attorney, Agent, or Firm—Wenderoth, Lind & Ponack, LLP

(57) ABSTRACT

Phenyl sulfamate derivatives represented by the following formula or salts thereof have a powerful inhibitory effect on steroid sulfatase and are hence useful for the prophylaxis or treatment of diseases associated with steroids such as estrogens, such as breast cancer, corpus uteri cancer, endometrial hyperplasia, infertility, endometriosis, adenomyosis uteri, autoimmune disease, dementia or Alzheimer's disease.

(I)

$$R^1\text{-}N(R^2)\text{-}S(=O)_2\text{-}O\text{-}C_6H_4(R^3)\text{-}A$$

wherein $R^1$ and $R^2$ each independently represent a hydrogen atom or a lower alkyl group; $R^3$ represents a hydrogen atom, a halogen atom, a lower alkyl group, $-OSO_2NR^1R^2$, a lower alkanoylamino group, a nitro group or a cyano group; and A represents a substituted or unsubstituted phenyl group, a group of the formula $-X-NR^4R^5$, or the like.

8 Claims, No Drawings

PHENYL SULFAMATE DERIVATIVES

TECHNICAL FIELD

This invention relates to novel phenyl sulfamate derivatives or salts thereof. More particularly, it relates to phenyl sulfamate derivatives represented by the following formula, or salts thereof.

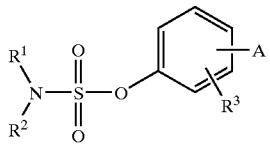

(I)

wherein $R^1$ and $R^2$ each independently represent a hydrogen atom or a lower alkyl group;

$R^3$ represents a hydrogen atom, a halogen atom, a lower alkyl group, —$OSO_2NR^1R^2$, a lower alkanoylamino group, a nitro group or a cyano group; and A represents a substituted or unsubstituted phenyl group, a naphthyl group, a pyridyl group, 2-substituted thiazol-4-yl group, 3-substituted isoxazol-5-yl group, 1-cyano-2-(substituted or unsubstituted phenyl)vinyl group, 2-cyano-2-(substituted or unsubstituted phenyl)vinyl group, or a group of the formula—X—$NR^4R^5$ [in which X represents CO or $CH_2$, $R^4$ represents a hydrogen atom, a lower alkyl group, a substituted or unsubstituted phenyl group, a lower alkanoyl group, a substituted or unsubstituted phenylcarbonyl group, a heteroarylcarbonyl group, a lower alkylsulfonyl group, a sulfamoyl group, a lower alkanoylamino group, a di(lower alkyl)amino group, a heteroaryl group, a heteroaryl-substituted lower alkyl group, or a substituted or unsubstituted phenylmethyl group, and $R^5$ represents a hydrogen atom, a substituted or unsubstituted phenyl group, or a substituted or unsubstituted phenylcarbonyl group, provided that ① when X represents CO, $R^4$ represents a group other than a lower alkanoyl group, a substituted or unsubstituted phenylcarbonyl group, a heteroarylcarbonyl group, a lower alkylsulfonyl group, and a sulfamoyl group, and $R^6$ represents a group other than a substituted or unsubstituted phenylcarbonyl group;

② when $R^4$ represents a lower alkanoyl group, a substituted or unsubstituted phenylcarbonyl group, a heteroarylcarbonyl group, a lower alkylsulfonyl group, or a sulfamoyl group, X represents $CH_2$ and $R^5$ represents a group other than a substituted or unsubstituted phenylcarbonyl group; and ③ when $R^5$ represents a substituted or unsubstituted phenylcarbonyl group, X represents $CH_2$ and $R^4$ represents a group other than a lower alkanoyl group, a substituted or unsubstituted phenylcarbonyl group, a heteroarylcarbonyl group, a lower alkylsulfonyl group, and a sulfamoyl group]; or $R^3$ and A, together with the phenyl group to which they are attached, represent a fluoren-2-yl or 9-oxofluoren-2-yl group; provided that, when $R^3$ represents a hydrogen atom, A does not represent an unsubstituted phenyl group.

BACKGROUND ART

Steroid sulfates such as dehydroepiandrosterone sulfate, cholesterol sulfate and estrone sulfate are intermediate products in the steroid metabolism within the human body. For example, estrone sulfate is hydrolyzed by steroid sulfatase present in the living body to yield estrone in free form. It is also known that, in the living body, this estrone is further converted reversibly into estradiol by the action of 17β-hydroxysteroid dehydrogenase. These estrogens formed in the steroid metabolism, such as estrone and estradiol are considered to be closely associated with diseases such as breast cancer, uterine cancer, ovarian cancer, endometriosis, adenomyosis uteri and mastopathy.

Accordingly, it is believed that, if the action of steroid sulfatase can be effectively inhibited, this would be effective for the treatment of diseases associated with steroids such as estrogens. From this point of view, several steroidal compounds having an inhibitory effect on steroid sulfatase, as typified by estrone 3-sulfamate (EMATE), have been proposed (see Published Japanese Translation of PCT International Publication No. 501515/'95).

However, although EMATE has a powerful inhibitory effect on steroid sulfatase, it also has a powerful estrogenic action and is hence a compound which is unsuitable for use as a drug for the treatment of diseases associated with estrogens.

Moreover, as nonsteroidal compounds having an inhibitory effect on steroid sulfatase, certain coumarin derivatives [e.g., 4-methylcoumarin 7-sulfamate (COUMATE)] have been proposed [see J. Med. Chem., Vol. 37, 219(1994)]. Furthermore, certain phenyl sulfamate derivatives [e.g., 4-(2-myristoylaminoethyl)phenyl sulfamate (DU-14)]have also been proposed [see J. Med. Chem., Vol. 39, 1349 (1996)]. In addition, steroid sulfatase inhibitors having a specific ring system and a sulfamoyloxy group are also known (see U.S. Pat. No. 6,011,024 and the pamphlet of International Publication of PCT Application No. WO2000/18397).

These nonsteroidal compounds such as COUMATE and DU-14 do not show an estrogenic action as a side effect. However, their principal action (i.e., their inhibitory effect on steroid sulfatase) is weak and, therefore, these compounds are not satisfactory as yet.

Japanese Patent Laid-Open No. 47162/'91 and U.S. Pat. No. 5,192,785 disclose certain sulfamate compounds. Although it is described therein that those compounds are useful as drugs for the treatment of chronic arthritis, osteoporosis, glaucoma and the like, neither mention nor suggestion is made of their inhibitory effect on steroid sulfatase.

The present inventors have now found that novel phenyl sulfamate derivatives in which the phenyl group is substituted by a specific substituent (e.g., substituted or unsubstituted phenyl, N-substituted aminomethyl or N-substituted carbamoyl), or salts thereof exhibit a powerful inhibitory effect on steroid sulfatase without showing an estrogenic action as a side effect.

Thus, the present invention provides phenyl sulfamate derivatives represented by the above formula (I), or salts thereof.

DISCLOSURE OF THE INVENTION

The term "lower" as used herein means that the group or compound modified by this term has 6 or less carbon atoms and preferably 4 or less carbon atoms.

Thus, examples of the "lower alkyl group" include methyl ethyl n-propyl isopropyl n-butyl isobutyl sec-butyl, tert-butyl and n-hexyl, and examples of the "lower alkoxy group" include methoxy, ethoxy, n-propoxy, isopropoxy, n-butoxy, isobutoxy and n-hexyloxy. Moreover, examples of the "lower alkylenedioxy group" include methylenedioxy, ethylenedioxy and trimethylenedioxy, and examples of the "lower alkanoyl group" include acetyl propionyl butyryl isobutyryl and pentanoyl.

The "lower alkanoylamino group" is an amino group substituted by the above-defined "lower alkanoyl group", and examples thereof include acetylamino, propionylamino and butyrylamino. The "di(lower alkyl)amino group" is an amino group di-substituted by the above-defined "lower alkyl group", and examples thereof include dimethylamino, diethylamino and dipropylamino. The "lower alkylsulfonyl group" is a sulfonyl group substituted by the above-defined "lower alkyl group", and examples thereof include methanesulfonyl and ethanesulfonyl.

"—$OSO_2NR^1R^2$" is a sulfamoyloxy group whose N atom may optionally be mono- or di-substituted by the above-defined "lower alkyl group". Examples thereof include, besides unsubstituted sulfamoyloxy, N-methylsulfamoyloxy, N,N-dimethylsulfamoyloxy and N,N-diethylsulfamoyloxy.

"—$NHSO_2NR^1R^2$" is a sulfamoylamino group whose N atom may optionally be mono- or di-substituted by the above-defined "lower alyl group". Examples thereof include, besides unsubstituted sulfamoylamino, N-methylsulfamoylamino, N,N-dimethylsulfamoylamino and N,N-diethylsulfamoylamino.

The "organic sulfonyloxy group" is a hydroxyl group substituted by an "organic sulfonyl group" which is a residue obtained by eliminating a hydroxyl group (OH) from an organic sulfonic acid, and preferred examples thereof include methanesulfonyloxy, p-toluenesulfonyloxy and benzenesulfonyloxy. The "organic sulfonylamino group" is an amino group substituted by the above-defined "organic sulfonyl group", and preferred examples thereof include methanesulfonylamino, p-toluenesulfonylamino and benzenesulfonylamino.

The "aralkyl group" is an alkyl group substituted by a monocyclic or polycyclic aryl group such as phenyl or naphthyl, and preferably an aryl-substituted lower alkyl group. Examples thereof include benzyl, 1-phenylethyl, 2-phenylethyl and 1-phenylpropyl.

In the "substituted or unsubstituted phenyl group" used in the definition of A, $R^4$ and $R^5$, examples of the substituent(s) on the phenyl group include halogen, lower alkyl, halogen-substituted lower alkyl cyano-substituted lower alkyl, hydroxyl, lower alkoxy, lower alkylenedioxy, lower alkanoyloxy, sulfamoyloxy, N-(lower alkyl)sulfamoyloxy, N,N-di(lower allyl)sulfamoyloxy, organic sulfonyloxy, amino, lower alkylamino, di(lower alkyl)amino, lower alkanoylamino, sulfamoyloxy, N-(lower alkyl)sulfamoyloxy, N,N-di(lower alkyl)sulfamoyl-oxy, organic sulfonylamino, aralkyloxycarbonylamino, lower alkoxycarbonylamino, mercapto, lower alkylthio, lower alkanoylthio, nitro, cyano, carboxyl and lower alkoxycarbonyl, and the phenyl group may be substituted by one to three substituents selected from the foregoing groups. Especially preferred examples of the substituted phenyl group are phenyl groups substituted by one or two substituents selected from halogen, lower alkyl, halogen-substituted lower alkyl cyano-substituted lower alkyl lower alkoxy, lower alkanoyloxy, —$OSO_2NR^1R^2$, organic sulfonyloxy, amino, lower alkanoylamino, —$NHSO_2NR^1R^2$, organic sulfonylamino, nitro, cyano, carboxyl and lower alkoxycarbonyl.

Moreover, in the "substituted or unsubstituted phenylcarbonyl group" used in the definition of $R^4$ and $R^5$, examples of the substituent(s) on the phenyl group include the same groups as described above for the "substituted or unsubstituted phenyl group", and the phenyl group may be substituted by one to three substituents selected from them. Especially preferred examples of the substituted phenylcarbonyl group are phenylcarbonyl groups whose phenyl group is substituted by one or two substituents selected from halogen, lower alkyl, lower alkoxy, sulfamoyloxy, nitro and cyano.

Furthermore, in the "substituted or unsubstituted phenylmethyl group" used in the definition of $R^4$, examples of the substituent(s) on the phenyl group include the same groups as described above for the "substituted or unsubstituted phenyl group", and the phenyl group may be substituted by one to three substituents selected from them. Especially preferred examples of the substituted phenylmethyl group are phenylmethyl groups whose phenyl group is substituted by one or two substituents selected from halogen, lower alkyl, lower alkoxy, sulfamoyloxy, nitro and cyano.

In the "2-substituted thiazol-4-yl or 3-substituted isoxazol-5-yl" used in the definition of A, examples of the substituent include lower alkyl, nitro and cyano.

In the "heteroarylcarbonyl group", "heteroaryl group" and "heteroaryl-substituted lower alkyl group" used in the definition of $R^4$, the term "heteroaryl" means a monocyclic or polycyclic unsaturated heterocyclic group which contains 1 to 4 heteroatoms selected from nitrogen, oxygen and sulfur atoms and which includes a five- to seven-membered ring. Alternatively, the heterocyclic ring may further be fused with an aromatic hydrocarbon ring to form a fused ring. Among such heteroaryl groups, preferred ones are five- or six-membered monocyclic heterocyclic groups containing 1 to 3 heteroatoms selected from nitrogen, oxygen and sulfur atoms.

Thus, examples of such "heteroaryl groups" include pyrrolyl, furyl, thienyl, imidazolyl, pirazolyl, oxazolyl, isoxazolyl, thiazolyl, triazolyl, thiadiazolyl, tetrazolyl, pyridyl, pyranyl, pyrimidinyl, pyridazinyl, pyrazinyl, azepinyl, purinyl, naphthyridinyl, pteridinyl, benzothienyl, benzofuranyl, indolyl, isoindolyl, indazolyl, benzimidazolyl, benzoxazolyl, benzothiazolyl, quinolyl, isoquinolyl, chromenyl, phthalazinyl, quinazolinyl, quinoxalinyl, carbazolyl, phenanthridinyl, acridinyl and dibenzazepinyl.

When A represents a group of the formula —X—$NR^4R^5$, and X, $R^4$ and/or $R^5$ have a —CO— or —$SO_2$— moiety attached directly to the N atom in this formula, this group should not contain more than one such moiety. Accordingly, in the group of the formula —X—$NR^4R^5$, ① when X represents CO, $R^4$ represents a group other than a lower alkanoyl group, a substituted or unsubstituted phenylcarbonyl group, a heteroarylcarbonyl group, a lower alkylsulfonyl group, and a sulfamoyl group, and $R^5$ represents a group other than a substituted or unsubstituted phenylcarbonyl group; ② when $R^4$ represents a lower alkanoyl group, a substituted or unsubstituted phenylcarbonyl group, a heteroarylcarbonyl group, a lower alkylsulfonyl group, or a sulfamoyl group, X represents $CH_2$ and $R^5$ represents a group other than a substituted or unsubstituted phenylcarbonyl group; and ③ when $R^5$ represents a substituted or unsubstituted phenylcarbonyl group, X represents $CH_2$ and $R^4$ represents a group other than a lower alkanoyl group, a substituted or unsubstituted phenylcarbonyl group, a heteroarylcarbonyl group, a lower alkylsulfonyl group, and a sulfamoyl group.

Moreover, the term "halogen atom" comprehends fluorine, chlorine, bromine and iodine atoms.

One preferred class of compounds in accordance with the present invention are the compounds of formula (I) in which both $R^1$ and $R^2$ represent hydrogen atoms.

Another preferred class of compounds in accordance with the present invention are the compounds of formula (I) in which $R^3$ represents a hydrogen atom or a halogen atom.

Still another preferred class of compounds in accordance with the present invention are the compounds of formula (I) in which A is located at the 4-position.

A further preferred class of compounds in accordance with the present invention are the compounds of formula (I) in which A represents a substituted phenyl group or a group of the formula —X—$NR^4R^5$.

Still a further preferred class of compounds in accordance with the present invention are the compounds of formula (I) in which the substituted phenyl group defined for A is a phenyl group substituted by one or two substituents selected from halogen, lower alkyl halogen-substituted lower alkyl, cyano-substituted lower alkyl, lower alkoxy, lower alkanoyloxy, —$OSO_2NR^1R^2$, organic sulfonyloxy, amino, lower alkanoylamino, —$OSO_2NR^1R^2$, organic sulfonylamino, nitro, cyano, carboxyl and lower alkoxycarbonyl.

Still a further preferred class of compounds in accordance with the present invention are the compounds of formula (I) in which, in the substituted phenyl group defined for A, the substituent or substituents are located at the 2- and/or 4-positions of the phenyl group.

Still a further preferred class of compounds in accordance with the present invention are the compounds of formula (I) in which A represents a group of the formula —X—$NR^4R^5$ and $R^4$ represents a hydrogen atom, a lower alkyl group or a heteroaryl group.

Still a further preferred class of compounds in accordance with the present invention are the compounds of formula (I) in which the heteroaryl group defined for $R^4$ is a five- or six-membered monocyclic heteroaryl group containing 1 to 3 nitrogen atoms.

Still a further preferred class of compounds in accordance with the present invention are the compounds of formula (I) in which $R^5$ represents a substituted phenyl group, such as a phenyl group substituted by one or two substituents selected from hydroxyl, lower alkanoyloxy, —$OSO_2NR^1R^2$, nitro and cyano.

In addition to the compounds described in the examples which will be given later, typical examples of the compounds of the above formula (I) which are provided by the present invention include:

2'-nitrobiphenyl-4-yl N-methylsulfamate,
2'-cyanobiphenyl-4-yl N,N-dimethylsulfamate,
4'-nitrobiphenyl-4-yl N,N-dimethylsulfamate,
4-[N-(4-cyanophenyl)-N-(1,2,4-triazol-4-yl)aminomethyl]phenyl N,N'-dimethylsulfamate,
2'-bromobiphenyl-4-yl sulfamate,
4'-methylbiphenyl-4-yl sulfamate,
4'-hydroxybiphenyl-4-yl sulfamate,
3',4'-methylenedioxybiphenyl-4-yl sulfamate,
4'-sulfamoyloxybiphenyl-4-yl acetate,
biphenyl-4,4'-diyl 4-(N,N-dimethylsulfamate) 4'-sulfamate,
4'-aminobiphenyl-4-yl sulfamate,
4'-acetylaminobiphenyl-4-yl sulfamate,
4'-dimethylaminobiphenyl-4-yl sulfamate,
4'-sulfamoyloxybiphenyl-4-carboxylic acid,
4'-methylthiobiphenyl-4-yl sulfamate,
2'-cyanobiphenyl-4,4'-diyl disulfamate,
2'-cyano-4'-trifluoromethylbiphenyl-4-yl sulfamate,
methyl 2'-cyano-4'-sulfamoyloxy-4-biphenylcarboxylate,
2'-cyano-4'-cyanomethylbiphenyl-4-yl sulfamate,
4-cyanobiphenyl-2,4'-diyl disulfamate,
biphenyl-2,4,4'-triyl trisulfamate,
3-chloro-2'-cyanobiphenyl-4-yl sulfamate,
3-chloro-4'-nitrobiphenyl-4-yl sulfamate,
3-chlorobiphenyl-4,4'-diyl disulfamate,
3-chloro-2'-cyano-4'-nitrobiphenyl-4-yl sulfamate,
2-methyl-2'-nitrobiphenyl-4-yl sulfamate,
2'-cyano-2,4'-dinitrobiphenyl-4-yl sulfamate,
2-nitrobiphenyl-4,4yl-4,4'-diyl disulfamate,
2,4'-dicyanobiphenyl-4-yl sulfamate,
4-(2-pyridyl)phenyl sulfamate,
4-(2-cyanothiazol-4-yl)phenyl sulfamate,
4-(3-methylisoxazol-5-yl)phenyl sulfamate,
4-[N-(4-sulfamoyloxyphenyl)aminomethyl]phenyl sulfamate,
methyl 4-[N-(4-sulfamoyloxybenzoyl)amino]benzoate,
4-[N-(4-bromophenyl)carbamoyl]phenyl sulfamate,
4-[N-(4-trifluoromethylphenyl)carbamoyl]phenyl sulfamate,
4-[N-(4-nitrophenyl)carbamoyl]phenyl sulfamate,
4-[N-(4-cyanomethylphenyl)carbamoyl]phenyl sulfamate,
4-[N-(2-cyano-4-nitrophenyl)carbamoyl]phenyl sulfamate,
4-[N-ethyl-N-(4-sulfamoyloxyphenyl)aminomethyl]phenyl sulfamate,
4-[N-(4-cyanophenyl)-N-(4-sulfamoyloxyphenyl)carbamoyl]phenyl sulfamate,
4-[N,N-di(4-sulfamoyloxyphenyl)carbamoyl]phenyl sulfamate,
4-[N-(4-acetyl-N-(4-cyanophenyl)aminomethyl]phenyl sulfamate,
4-[N-benzoyl-N-(4-sulfamoyloxybenzyl)amino]phenyl sulfamate,
4-(sulfamoylaminomethyl)phenyl sulfamate,
4-[N'-acetyl-N-(4-sulfamoyloxyphenyl)hydrazinocarbonyl]phenyl sulfamate,
4-(N',N'-dimethyl-N-phenylhydrazinocarbonyl)phenyl sulfamate,
4-[N-(4-sulfamoyloxyphenyl)-N-(1,2,4-triazol-4-yl)carbamoyl]-phenyl sulfamate,
4-[N-(2-nitrophenyl)-N-(1,2,4-triazol-4-yl)carbamoyl]phenyl sulfamate,
4-[N-(4-nitrophenyl)-N-(1,2,4-triazol-4-yl)aminomethyl]phenyl sulfamate,
4-[N-(2-cyanophenyl)-N-(1,2,4-triazol-4-yl)aminomethyl]phenyl sulfamate,
4-[N-(4-cyanophenyl)-N-(pyrazol-1-yl)aminomethyl]phenyl sulfamate,
4-[N-(4-cyanophenyl)-N-(imidazol-1-yl)aminomethyl]phenyl sulfamate,
4-[N-(4-cyanophenyl)-N-(tetrazol-1-yl)aminomethyl]phenyl sulfamate,
4-[N-benzoyl-N-ethylaminomethyl]phenyl sulfamate,
2-chloro-4-[N-(4-cyanophenyl)-N-(1,2,4-triazol-4-yl)aminomethyl]phenyl sulfamate,
4-[N-(4-cyanophenyl)-N-(1,2,4-triazol-4-yl)aminomethyl]-3-nitrophenyl sulfamate,
2'-cyanobiphenyl-3-yl sulfamate biphenyl-3,4'-diyl disulfamate, and
2'-cyano-4'-nitrobiphenyl-3-yl sulfamate.

Depending on the type of substituent A, the compounds of formula (I) in accordance with the present invention may optionally form salts. Examples of such salts include salts formed with inorganic acids such as hydrochloric acid, hydrobromic acid, sulfuric acid, nitric acid and phosphoric acid; salts formed with organic acids such as acetic acid, oxalic acid, citric acid, lactic acid, tartaric acid and p-toluenesulfonic acid; alkali metal salts such as sodium, potassium and lithium salts; alkaline earth metal salts such as calcium and magnesium salts; salts formed with organic bases such as triethylamine, dicyclohexylamine, pyrrolidine, morpholine and pyridine; and ammonium salts. Among others, pharmaceutically acceptable salts are preferred.

According to the present invention, the compounds of the above formula (I) may be prepared, for example, by reacting an phenol derivative of the formula

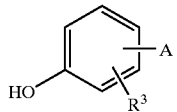
(II)

wherein A and $R^3$ have the above-defined meanings, with an amidosulfonic acid chloride of the formula

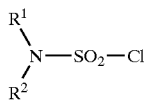
(III)

wherein $R^1$ and $R^2$ have the above-defined meanings.

This reaction may generally be carried out in an inert solvent selected, for example, from amides such as N,N-dimethylformamide and N-methylpyrrolidone; alkyl halides such as dichloromethane and dichloroethane; and organic bases such as pyridine, optionally in the presence of an alkali such as sodium hydride, sodium methoxide, potassium butoxide, potassium hydroxide or potassium phosphate, or an organic base such as triethylamine or 2,6-di-tert-butyl-4-methylpyridine, at a temperature ranging from about –20° C. to the reflex temperature of the reaction mixture and preferably from about 0° C. to room temperature.

No particular limitation is placed on the proportion of the amidosulfonic acid chloride of formula (III) to the compound of formula (II). However, the amidosulfonic acid chloride may generally be used in an amount of at least 1 mole, preferably about 1.1 to 20 moles, and more preferably about 2 to 10 moles, per mole of the compound of formula (II). Moreover, the aforesaid alkali is suitably used in an amount of about 2 to about 10 moles per mole of the compound of formula (II).

The compounds of the above formula (I) in which both $R^1$ and $R^2$ represent hydrogen atoms may also be prepared by reacting a phenol derivative of the above formula (II) with chlorosulfonyl isocyanate and then treating the resulting product with water.

The aforesaid reaction of the phenol derivative of formula (II) with chlorosulfonyl isocyanate may generally be carried out in an inert solvent selected, for example, from aromatic hydrocarbons such as toluene and xylene; halogenated aromatic hydrocarbons such as chlorobenzene and dichlorobenzene; and acetonitrile, at a temperature ranging from 50° C. to the reflex temperature of the reaction mixture and preferably from 80° C. to the reflex temperature of the reaction mixture.

No particular limitation is placed on the proportion of chlorosulfonyl isocyanate to the phenol derivative of formula (II). However, chlorosulfonyl isocyanate may generally be used in an amount of at least 1 mole and preferably about 1.01 to 2 moles, per mole of the compound of formula (II).

The subsequent treatment with water may usually be carried out simply by adding water to the reaction mixture resulting from the aforesaid reaction.

The compounds of the above formula (I) in which X represents $CH_2$, $R^5$ represents a hydrogen atom, and $R^4$ represents a group other than a lower alkanoyl group, a substituted or unsubstituted phenylcarbonyl group, a heteroarylcarbonyl group, a lower alkylsulfonyl group, and a sulfamoyl group may also be prepared, for example, by reacting an aldehyde compound of the formula

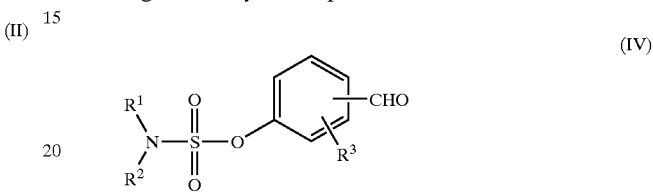
(IV)

wherein $R^1$, $R^2$ and $R^3$ have the above-defined meanings, with an amino compound of the formula

(V)

wherein $R^{41}$ represents a hydrogen atom, a lower alkyl group, a substituted or unsubstituted phenyl group, a lower alkanoylamino group, a di(lower alkyl)amino group, a heteroaryl group, a heteroaryl-substituted lower alkyl group, or a substituted or unsubstituted phenylmethyl group; and reducing the Schiff base so formed.

The aforesaid reaction of the aldehyde compound of formula (IV) with the amino compound of formula (V) may generally be carried out in the absence of solvent, or in a solvent selected from water; alcohols such as methanol and ethanol; ethers such as diethyl ether, tetrahydrofuran, dimethoxyethane and dioxane; alkanoic acids such as acetic acid and propionic acid; and amides such as dimethylformamide and dimethylacetamide, at a temperature ranging from 0° C. to the reflex temperature of the reaction mixture and preferably from room temperature to 100° C.

No particular limitation is placed on the proportion of the amino compound of formula (V) to the aldehyde compound of formula (IV). However, the amino compound of formula (V) may generally be used in an amount of at least 1 mole, preferably about 1.1 to 20 moles, and more preferably about 2 to 10 moles, per mole of the compound of formula (IV).

The reduction of the Schiff base may usually be carried out simply by adding a complex metal hydride (e.g., sodium borohydride or sodium cyanoborohydride) to the reaction mixture containing the Schiff base formed and reacting this mixture at a reaction temperature ranging from about 0° C. to room temperature.

Thus, the compounds of the above formula (I) which are desired in the present invention can be formed.

Among the compounds of the above formula (II) which are used as starting materials in the aforesaid reactions, most of the compounds in which A represents a substituted or unsubstituted phenyl group, a naphthyl group, a pyridyl group, a 4-substituted thiazol-2-yl group, a 3-substituted isoxazol-5-yl group, a 1-cyano-2-(substituted or unsubstituted phenyl)vinyl group, or a 2-cyano-2-(substituted or unsubstituted phenyl)vinyl group are known compounds described in the literature of the prior art. In the case of novel compounds, they may be easily prepared in the same manner as the known compounds. For example, the compounds of formula (II) in which A represents a substituted phenyl group may be prepared by reacting a substituted phenyl halide compound with a 4-methoxyphenylboric acid compound and eliminating the hydroxyl-protecting group of the resulting substituted anisole compound with the aid of a Lewis acid (e.g., boron tribromide or aluminum chloride) or an acid (e.g., hydrobromic acid). For details on the reaction conditions and the like, refer to Preparation Examples 1 and 2 which will be given later.

On the other hand, most of the compounds of the above formula (II) in which A represents —X—NR$^4$R$^5$ are novel compound which have not been described in the literature of the prior art. Depending on the type of the substituent R$^5$, they may be prepared, for example, by following the pathway shown in Reaction Scheme 1 or 2 given below. For details on the reaction conditions and the like, refer to Preparation Examples 7–11, 14, 20, 22, 23, 25, 28, 29, 31, 34, 35, 38, 47 and 52 which will be given later.

When R$^5$ represents a hydrogen atom or a substituted or unsubstituted phenyl group:

Reaction Scheme 1

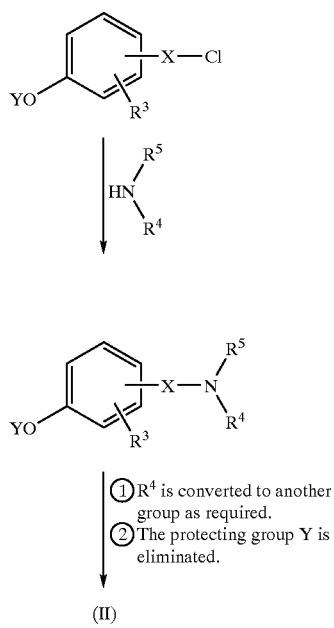

In the above formulas, Y represents a hydroxyl-protecting group; and X, R$^3$, R$^4$ and R$^5$ have the above-defined meanings.

When R$^5$ represents a substituted or unsubstituted phenylcarbonyl group:

Reaction Scheme 2

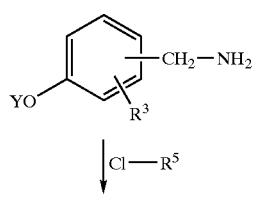

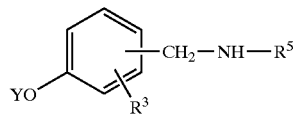

① Hydrogen atoms are converted to other R$^4$ groups as required.
② The protecting group Y is eliminated.

(II)

In the above formulas, Y, R$^3$, R$^4$ and R$^5$ have the above-defined meanings.

Moreover, most of the aldehyde compounds of the above formula (IV) which are used as starting materials in the aforesaid reaction are novel compounds which have not been described in the literature of the prior art. They may be easily prepared, for example, by reacting an aldehyde compound of the formula

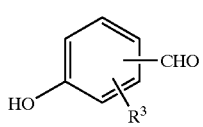

wherein R$^3$ has the above-defined meaning, with an amidosulfonic acid chloride of the above formula (III) in the same manner as described in connection with the reaction of a compound of the above formula (II) with an amidosulfonic acid chloride of the above formula (III). For details on the reaction conditions of this reaction, and the like, refer to Preparation Example 24 which will be given later.

When the compounds used in each of the aforesaid reactions contain substituents (e.g., hydroxyl, amino and carboxyl) which may participate in the reaction, these substituents may be protected by protecting groups as required. These protected by protecting groups may be eliminated after completion of the reaction.

Thus, the compounds of the above formula (I) which are formed according to the processes of the present invention may be isolated and purified from the reaction mixture by per se known techniques such as recrystallization, distillation, column chromatography and thin-layer chromatography.

The above-described phenyl sulfamate derivatives of formula (I) or salts thereof in accordance with the present invention have a powerful inhibitory effect on steroid sulfatase and are hence effective for the treatment of diseases associated with steroids (e.g., estrogens), such as breast cancer, corpus uteri cancer, ovarian cancer, endometrial hyperplasia, infertility, endometriosis, adenomyosis uteri, hysteromyoma, autoimmune diseases, dementia, Alzheimer's disease, mastopathy, gynecomastia in the male, prostatomegaly, and male infertility due to oligospermia.

The inhibitory effect on steroid sulfatase of compounds of formula (I) in accordance with the present invention can be measured according to the following procedure.

(1) Measurement of an In vitro Inhibitory Effect on Steroid Sulfatase

Six-well plates (9.4 cm$^2$/well) were inoculated with intact MCF-7 human breast cancer cells at a density of about 1×10$^5$ cells/well. Using Dulbecco's modified Eagle medium (DMEM) containing 10 mM HEPES, 5% fetal bovine serum, 0.011% sodium pyruvate and 0.37% sodium bicarbonate, the cells were grown to 80% confluency.

The plates were washed with Earle's balanced salt solution (EBSS from Life Technologies Inc., Grand Island, N.Y., USA). Then, serum-free DMEM (2 ml) containing 4 pmol (4.4×10$^5$ dpm) of [6,7-$^3$H]estrone 3-sulfate (with a specific activity of 49 Ci/mmol; from New England Nuclear, Boston, Mass., USA), together with a test compound, was placed on each plate and incubated at 37° C. for 20 hours. After incubation, the plate was cooled, and the medium (1 ml) was pipetted into a separating tube containing [4-$^{14}$C]estrone (6×10$^3$ dpm) (with a specific activity of 52.5 mCi/mmol; from New England Nuclear, Boston, Mass., USA). This mixture, together with toluene (4 ml), was vigorously shaken for 30 seconds. It was shown by experiment that more than 90% of [4-$^{14}$C]estrone was removed from the aqueous layer by this treatment. A portion (2 ml) of the organic phase was taken, and the $^3$H and $^{14}$C contents thereof were measured by scintillation spectrometry. Then, the amount of estrone 3-sulfate hydrolyzed was calculated from the total 3H count (corrected for the volumes of the medium used and the organic phase, and for the recovery of the [$^{14}$C]estrone added) and the specific activity of the substrate. The results thus obtained are shown in the following Table 1.

TABLE 1

| Example No. of compound | Inhibitory rate (3 × 10$^{-9}$ M. %) |
| --- | --- |
| Example 3 | 76 |
| Example 23 | 67 |
| Example 25 | 87 |
| Example 27 | 94 |

(2) Measurement of an In vivo Inhibitory Effect on Steroid Sulfatase

A test compound was suspended in a 0.5% polyoxyethylene (20) sorbitan monooleate solution (Tween 80) and administered, once a day, to a group of 5 female SD strain rats (weighing 168–194 g) for 5 days.

Four hours after the final administration, all rats were sacrificed by ether anesthesia and dissected. Thus, the liver and the uterus were excised from each rat, washed once with cold phosphate-buffered saline (PBS, pH 7.4), and preserved at −70° C. or below. Each of the liver and the uterus was finely minced with scissors, and suspended in PBS containing 250 mM sucrose (5 ml/g tissue). Under cooling with ice, each suspension was homogenized with an Ultra-Turrax homogenizer. The resulting homogenate was centrifuged (at 4° C.) at 2,000×g for 30 minutes to remove nuclei and cell debris, and the protein concentration in this supernatant was measured according to the method of Bradford [Anal. Biochem. 72, 248–254(1976)].

The homogenate in an amount corresponding to a protein concentration of 100–500 μg/ml was mixed with [6,7-$^3$H] estrone 3-sulfate (with a specific activity of 49 Ci/mmol; from New England Nuclear, Boston, Mass., USA) in an amount corresponding to a substrate concentration of 20 μM. This mixture was diluted with PBS to a total volume of 1 ml, and incubated at 37° C. for 30 minutes. After incubation (1 ml), the steroid sulfatase activity was determined in the same manner as described above for the in vitro measurement (1). The results thus obtained are shown in the following Table 2.

TABLE 2

| Example No. of compound | Inhibitory rate (0.5 mg/kg, p.o., %) | |
| --- | --- | --- |
| | Liver | Uterus |
| Example 1 | 91.2 | 94.9 |
| Example 3 | 95.4 | 93.8 |
| Example 16 | 97.0 | 100 |
| Example 21 | 97.2 | 97.6 |
| Example 25 | 99.5 | 100 |
| Example 38 | 85.3 | 79.0 |

Thus, the compounds of formula (I) or salts thereof in accordance with the present invention are useful as steroid sulfatase inhibitors and can hence be used for therapeutic purposes in human beings and other mammals by oral or parenteral administration (e.g., intramuscular injection, intravenous injection, intrarectal administration or percutaneous administration).

When the compounds of the present invention are used as drugs, they may be made into in any of various pharmaceutical preparations (or pharmaceutical compositions) according to the intended purpose. These pharmaceutical preparations include solid preparations (e.g., tablets, hard capsules, soft capsules, granules, powders, fine subtilaes, pills and troches), semisolid preparations (e.g., suppositories and ointments), and liquid preparations (e.g., injections, emulsions, suspensions, lotions and sprays). Pharmaceutically acceptable adjuvants which can be used in the aforesaid pharmaceutical preparations include, for example, starch, gelatin, glucose, lactose, fructose, maltose, magnesium carbonate, talc, magnesium stearate, methylcellulose, carboxymethylcellulose or salts thereof, acacia, polyethylene glycol, alkyl esters of p-hydroxybenzoic acid, syrup, ethanol propylene glycol petrolatum, carbowax, glycerin, sodium chloride, sodium sulfite, sodium phosphate and citric acid. The aforesaid pharmaceutical preparations may also contain other therapeutically useful drugs.

The content of the compounds of the present invention in the aforesaid pharmaceutical preparations may vary according to the dosage form. Generally, it is desirable that solid and semisolid preparations contain the compounds of the present invention at a concentration of 0.1 to 50% by weight and liquid preparations contain them at a concentration of 0.05 to 10% by weight.

The dosage of the compounds of the present invention may vary widely according to the type of the warm-blooded animal (including human being) to be treated, the route of administration, the severity of symptoms, the diagnosis made by the doctor, and the like. Generally, they may be administered in a daily dose of 0.01 to 5 mg/kg and preferably 0.02 to 2 mg/kg. However, it is a matter of course that they may be administered in doses less than the lower limit of the aforesaid range or greater than the upper limit thereof, depending on the severity of symptoms in the patient and the diagnosis made by the doctor. The aforesaid daily dose may be given at a time or in several divided doses.

EXAMPLES

The present invention is more specifically explained with reference to the following examples and preparation examples.

Example 1

108 mg of 2'-nitrobiphenyl-4-ol was dissolved in 1.5 ml of N,N-dimethyformamide, and a suspension of 120 mg of sodium hydride in 1.5 ml of N,N-dimethyformamide was added thereto under cooling with ice, followed by stirring for 10 minutes under cooling with ice. 367 mg of sulfamoyl chloride was added to this mixture, followed by stirring at room temperature for 3 hours. After water was added to the reaction mixture, the product was extracted with ethyl acetate. The organic layer was washed with water and dried over anhydrous magnesium. sulfate. After the solvent was distilled off, the resulting crude product was purified by TLC (using a 1:1 mixture of ethyl acetate and hexane as the developing solvent) to obtain 106 mg of 2'-nitrobiphenyl-4-yl sulfamate.

$^1$H-NMR(CDCl$_3$, δ): 5.07(2H, br s), 7.30–8.00(8H, m).

MS(m/z): 294(M$^+$), 215.

Example 2

108 mg of 2'-nitrobiphenyl-4-ol was dissolved in 9.5 ml of methylene chloride, and 312 mg of 2,6-di-tert-butyl-4-methylpyridine and 347 mg of sulfamoyl chloride were successively added thereto under cooling with ice, followed by stirring at room temperature for 5 hours. After water was added to the reaction mixture, the product was extracted with ethyl acetate. The organic layer was washed with water and dried over anhydrous magnesium sulfate. After the solvent was distilled off, the resulting crude product was purified by TLC (using a 1:1 mixture of ethyl acetate and hexane as the developing solvent) to obtain 149 mg of 2'-nitrobiphenyl-4-yl sulfamate.

Example 3

The procedure of Example 1 was repeated, except that 27 mg of 4'-hydroxy-2-biphenylcarbonitrile was used in place of 2'-nitrobiphenyl-4-ol. Thus, there was obtained 34 mg of 2'-cyanobiphenyl-4-yl sulfamate.

$^1$H-NMR(CDCl$_3$, δ): 5.02(2H, br s), 7.34–7.91(8H, m).

MS(m/z): 274(M$^+$), 195.

Example 4

The procedure of Example 1 was repeated, except that 79 mg of 2'-fluorobiphenyl-4-ol was used in place of 2'-nitrobiphenyl-4-ol. The resulting crude product was purified by TLC (using a 2:1 mixture of hexane and ethyl acetate as the developing solvent) to obtain 81 mg of 2'-fluorobiphenyl-4-yl sulfamate.

$^1$H-NMR(CDCl$_3$, δ): 4.95(2H, br s), 7.00–7.71(8H, m).

MS(m/z): 267(M$^+$), 188.

Example 5

The procedure of Example 1 was repeated, except that 45 mg of 2'-trifluoromethylbiphenyl-4-ol was used in place of 2'-nitrobiphenyl-4-ol. The resulting crude product was purified by TLC (using a 2:1 mixture of hexane and ethyl acetate as the developing solvent) to obtain 24 mg of 2'-trifluoromethylbiphenyl-4-yl sulfamate.

$^1$H-NMR(CDCl$_3$, δ): 4.96(2H, br 8), 7.26–7.85(8H, m).

MS(m/z): 317(M$^+$), 238.

Example 6

The procedure of Example 1 was repeated, except that 64 mg. of 2'-methylbiphenyl-4-ol was used in place of 2'-nitrobiphenyl-4-ol. The resulting crude product was purified by TLC (using a 2:1 mixture of hexane and ethyl acetate as the developing solvent) to obtain 51 mg of 2'-methylbiphenyl-4-yl sulfamate.

$^1$H-NMR(CDCl$_3$, δ): 2.26(3H, s), 4.97(2H, br s), 7.10–7.32(4H, m), 7.37(4H, s).

MS(m/z): 263(M$^+$), 184.

Example 7

The procedure of Example 2 was repeated, except that 37 mg of biphenyl-2,4'-diol was used in place of 2'-nitrobiphenyl-4-ol. The resulting crude product was purified by TLC (using a 10:1 mixture of chloroform and methanol as the developing solvent) to obtain 17 mg of biphenyl-2,4'-diyl disulfamate.

$^1$-NMR(CDCl$_3$, δ): 7.14–7.68(8H, m).

MS(m/z): 344(M$^+$), 265, 186.

Example 8

The procedure of Example 2 was repeated, except that 25 mg of 4'-hydroxy-2-biphenylacetonitrile was used in place of 2'-nitrobiphenyl-4-ol. Thus, there was obtained 30 mg of 2'-cyanomethylbiphenyl-4-yl sulfamate.

$^1$H-NMR(CDCl$_3$, δ): 3.64(2H, s), 7.15–7.63(8H, m).

MS(m/z): 288(M$^+$), 209.

Example 9

The procedure of Example 1 was repeated, except that 79 mg of 3'-fluorobiphenyl-4-ol was used in place of 2'-nitrobiphenyl-4-ol. The resulting crude product was purified by TLC (using a 2:1 mixture of hexane and ethyl acetate as the developing solvent) to obtain 72 mg of 3'-fluorobiphenyl-4-yl sulfamate.

$^1$H-NMR(CDCl$_3$, δ): 4.94(2H, br 8), 6.90–7.71(8H, m).

MS(m/z): 267(M$^+$), 188.

Example 10

The procedure of Example 1 was repeated, except that 49 mg of 3'-nitrobiphenyl-4-ol was used in place of 2'-nitrobiphenyl-4-ol. Thus, there was obtained 40 mg of 3'-nitrobiphenyl-4-yl sulfamate.

$^1$H-NMR(CDCl$_3$, δ): 7.33–7.78(5H, m), 7.79–7.98(1H, m), 8.11–8.33(1H, m), 8.33–8.50(1H, m).

MS(m/z): 294(M$^+$), 215.

Example 11

The procedure of Example 1 was repeated, except that 66 mg of 4'-hydroxy-3-biphenylcarbonitrile was used in place of 2'-nitrobiphenyl-4-ol. Thus, there was obtained 55 mg of 3'-cyanobiphenyl-4-yl sulfamate.

$^1$H-NMR(CDCl$_3$, δ): 5.07(2H, br s), 7.34–8.06(8H, m).

MS(m/z): 274(M$^+$), 195.

Example 12

The procedure of Example 1 was repeated, except that 40 mg of 4'-hydroxy-3-biphenylacetonitrile was used in place of 2'-nitrobiphenyl-4-ol. The resulting crude product was purified by TLC (using a 19:1 mixture of chloroform and methanol as the developing solvent) to obtain 15 mg of 3'-cyanomethylbiphenyl-4-yl sulfamate.

$^1$H-NMR(CD$_3$OD, δ): 3.97(2H, s), 7.34–7.78(8H, m).

MS(m/z): 288(M$^+$), 209.

Example 13

The procedure of Example 1 was repeated, except that 125 mg of 4'-bromobiphenyl-4-ol was used in place of 2'-nitrobiphenyl-4-ol. The resulting crude product was purified by TLC (using a 2:1 mixture of hexane and ethyl acetate as the developing solvent) to obtain 123 mg of 4'-bromobiphenyl-4-yl sulfamate.

$^1$H-NMR(CDCl$_3$, δ): 7.33–7.71(8H, m).

MS(m/z): 329(M$^+$+2), 327(M$^+$), 249, 247.

Example 14

The procedure of Example 1 was repeated, except that 102 mg of 4'-chlorobiphenyl-4-ol was used in place of 2'-nitrobiphenyl-4-ol. The resulting crude product was purified by TLC (using a 2:1 mixture of hexane and ethyl acetate as the developing solvent) to obtain 111 mg of 4'-chlorobiphenyl-4-yl sulfamate.

$^1$H-NMR(CDCl$_3$, δ): 4.99(2H, br s), 7.30–7.68(8H, m).

MS(m/z): 285(M$^+$+2), 283(M$^+$), 205, 203.

Example 15

The procedure of Example 1 was repeated, except that 100 mg of 4'-methoxybiphenyl-4-ol was used in place of 2'-nitrobiphenyl-4-ol. The resulting crude product was purified by TLC (using a 2:1 mixture of hexane and ethyl acetate as the developing solvent) to obtain 96 mg of 4'-methoxybiphenyl-4-yl sulfamate.

$^1$H-NMR(CDCl$_3$, δ): 3.86(3H, s), 6.98 (2H, d, J=5.8 Hz), 7.35–7.67 (6H, m).

MS(m/z): 279(M$^+$), 199.

Example 16

The procedure of Example 1 was repeated, except that 108 mg of 4'-nitrobiphenyl-4-ol was used in place of 2'-nitrobiphenyl-4-ol. Thus, there was obtained 108 mg of 4'-nitrobiphenyl-4-yl sulfamate.

$^1$H-NMR(CDCl$_3$, δ): 7.33–7.83(6H, m), 8.30(2H, d, J=6.0 Hz).

MS(m/z): 294(M$^+$), 215.

Example 17

The procedure of Example 1 was repeated, except that 228 mg of methyl 4'-hydroxy-4-biphenylcarboxylate was used in place of 2'-nitrobiphenyl-4-ol. Thus, there was obtained 27 mg of methyl 4'-sulfamoyloxy-4-biphenylcarboxylate.

MS(m/z): 307(M$^+$), 227.

Example 18

The procedure of Example 1 was repeated, except that 500 mg of 4'-hydroxy-4-biphenylcarbonitrile was used in place of 2'-nitrobiphenyl-4-ol. The resulting crude product was purified by TLC (using a 8:1 mixture of chloroform and ethyl acetate as the developing solvent) to obtain 489 mg of 4'-cyanobiphenyl-4-yl sulfamate.

$^1$H-NMR(DMSO-d$_6$, δ): 7.41(2H, d, J=5.5 Hz), 7.86(2H, d, J=5.5 Hz), 7.93(4H, s), 8.06(2H, br s).

MS(m/z): 274(M$^+$), 195.

Example 19

The procedure of Example 1 was repeated, except that 50 mg of 4'-trifluoromethylbiphenyl-4-ol was used in place of 2'-nitrobiphenyl-4-ol. The resulting crude product was purified by TLC (using a 2:1 mixture of hexane and ethyl acetate as the developing solvent) to obtain 35 mg of 4'-trifluoromethylbiphenyl-4-yl sulfamate.

$^1$H-NMR(CDCl$_3$, δ): 4.96(2H, br s), 7.43(2H, d, J=6.0 Hz), 7.62(2H, d, J=6.0 Hz), 7.67(4H, s).

MS(m/z): 317(M$^+$), 238.

Example 20

The procedure of Example 1 was repeated, except that 13 mg of 4'-hydroxy-4-biphenylacetonitrile was used in place of 2'-nitrobiphenyl-4-ol. The resulting crude product was purified by TLC (using a 19:1 mixture of chloroform and methanol as the developing solvent) to obtain 8 mg of 4'-cyanomethylbiphenyl-4-yl sulfamate.

$^1$H-NMR(CD$_3$OD, δ): 3.93(2H, s), 7.24–7.82(8H, m).

MS(m/z): 288(M$^+$), 209.

Example 21

The procedure of Example 1 was repeated, except that 50 mg of biphenyl-4,4'-diol was used in place of 2'-nitrobiphenyl-4-ol. Thus, there was obtained 52 mg of biphenyl-4,4'-diyl disulfamate.

$^1$H-NMR(CD$_3$OD, δ): 7.42(4H, d, J=5.8 Hz), 7.66(4H, d, J=5.8 Hz).

MS(m/z): 344(M$^+$), 265, 186.

Example 22

The procedure of Example 1 was repeated, except that 23 mg of 2-nitrobiphenyl-4,4'-diol was used in place of 2'-nitrobiphenyl-4-ol. The resulting crude product was purified by TLC (using a 10:1 mixture of chloroform and methanol as the developing solvent) to obtain 9 mg of 2-nitrobiphenyl-4,4'-diyl disulfamate.

$^1$H-NMR(CD$_3$OD, δ): 6.97–7.43(7H, m).

MS(m/z): 389(M$^+$), 310, 231.

Example 23

The procedure of Example 1 was repeated, except that 48 mg of 2',4'-dinitrobiphenyl-4-ol was used in place of 2'-nitrobiphenyl-4-ol. The resulting crude product was purified by TLC (using a 5:1 mixture of chloroform and tetrahydrofuran as the developing solvent) to obtain 42 mg of 2',4'-dinitrobiphenyl-4-yl sulfamate.

$^1$H-NMR(CDCl$_3$, δ): 7.32–7.55(4H, m), 7.66(1H, d, J=5.3 Hz), 8.49(1H, dd, J=1.5, 5.3 Hz), 8.74(1H, d, J=1.5 Hz).

MS(m/z): 339(M$^+$), 260.

Example 24

The procedure of Example 1 was repeated, except that 55 mg of 2,2'-dinitrobiphenyl-4,4'-diol was used in place of 2'-nitrobiphenyl-4-ol. The resulting crude product was purified by TLC (using a 10:1 mixture of chloroform and methanol as the developing solvent) to obtain 12 mg of 2,2'-dinitrobiphenyl-4,4'-diyl disulfamate.

$^1$H-NMR(CD$_3$OD, δ): 7.48(2H, d, J=5.7 Hz), 7.73(2H, dd, J=1.7, 5.7 Hz), 8.19(2H, d, J=1.5 Hz).

MS(m/z): 355(M$^+$—SO$_2$NH), 276.

Example 25

The procedure of Example 2 was repeated, except that 41 mg of 4'-hydroxy-4-nitro-2-biphenylcarbonitrile was used in place of 2'-nitrobiphenyl-4-ol. Thus, there was obtained 40 mg of 2'-cyano-4'-nitrobiphenyl-4-yl sulfamate.

$^1$H-NMR(CDCl$_3$, δ): 7.40–7.73(4H, m), 7.:74(11H, d, J=5.8 Hz), 8.51(1H, dd, J=1.5, 5.5 Hz), 8.65(1H, d, J=1.5 Hz).

MS(m/z): 319(M$^+$), 240.

Example 26

The procedure of Example 2 was repeated, except that 132 mg of 4'-hydroxy-2-nitro-4-biphenylcarbonitrile was used in place of 2'-nitrobiphenyl-4-ol. The resulting crude product was purified by TLC (using a 10:1 mixture of chloroform and methanol as the developing solvent) to obtain 116 mg of 4'-cyano-2'-nitrobiphenyl-4-yl sulfamate.

$^1$H-NMR(CDCl$_3$, δ): 7.33–7.70(4H, m), 7.60(1H, d, J=5.3 Hz), 7.92(1H, dd, J=1, 5.3 Hz), 8.19(1H, d, J=1 Hz).

MS(m/z): 319(M$^+$), 240.

Example 27

The procedure of Example 2 was repeated, except that 68 mg of 4'-hydroxy-2,4-biphenyldicarbonitrile was used in place of 2'-nitrobiphenyl-4-ol. The resulting crude product was purified by TLC (using a 15:1 mixture of chloroform and methanol as the developing solvent) to obtain 44 mg of 2',4'-dicyanobiphenyl-4-yl sulfamate.

$^1$H-NMR(CD$_3$OD, δ): 7.39–7.78(4H, m), 7.76(1H, d, J=5.5 Hz), 8.06(1H, dd, J=1.7, 5.5 Hz), 8.28(1H, d, J=1.7 Hz).

MS(m/z): 299(M$^+$), 220.

Example 28

The procedure of Example 1 was repeated, except that 90 mg of 4-[N-(4-hydroxybenzyl)amino]phenol was used in place of 2'-nitrobiphenyl-4-ol. The resulting crude product was purified by TLC (using a 6:1 mixture of chloroform and methanol as the developing solvent) to obtain 49 mg of 4-[N-sulfamoyl-N-(4-sulfamoyloxybenzyl)amino]phenyl sulfamate.

$^1$H-NMR(DMSO-d$_6$, δ): 4.77(2H, s), 7.0–8.1(14H, m).

SIMS(m/z): 453(MH$^+$).

Example 29

The procedure of Example 1 was repeated, except that 22 mg of N-(4-hydroxybenzyl)-N-(4-hydroxyphenyl)methanesulfonamide was used in place of 2'-nitrobiphenyl-4-ol. The resulting crude product was purified by TLC (using a 9:1 mixture of chloroform and methanol as the developing solvent) to obtain 12 mg of 4-[N-methylsulfonyl-N-(4-sulfamoyloxybenzyl)amino]phenyl sulfamate.

$^1$H-NMR(DMSO-d$_6$, δ): 3.09(3H, s), 4.89(2H, s), 7.1–8.1 (12H, m).

SIMS(m/z): 452(MH$^+$).

Example 30

The procedure of Example i was repeated, except that 60 mg of N-(4-hydroxybenzyl)-N-(4-hydroxyphenyl)acetamide was used in place of 2'-nitrobiphenyl-4-ol. The resulting crude product was purified by TLC (using a 9:1 mixture of chloroform and methanol as the developing solvent) to obtain 61 mg of 4-[N-acetyl-N-(4-sulfamoyloxybenzyl)amino]-phenyl sulfamate.

$^1$H-NMR(CDCl$_3$, δ): 1.90(3H, br s), 4.86(2H, s), 6.9–7.4 (8H, m).

HR-SIMS(m/z): 416.0582(MH$^+$).

Example 31

The procedure of Example 1 was repeated, except that 96 mg of 4-[N-acetyl-N-(4-hydroxybenzyl)amino]phenyl acetate was used in place of 2'-nitrobiphenyl-4-ol. The resulting crude product was purified by TLC (using a 4:1 mixture of chloroform and acetone as the developing solvent) to obtain 57 mg of 4-[N-acetyl-N-(4-sulfamoyloxybenzyl)amino]-phenyl acetate.

$^1$H-NMR(CDCl$_3$, δ): 1.89(3H, br s), 2.28(3H, s), 4.85(2H, s), 6.9–7.4(8H, m).

MS(m/z): 378(M$^+$), 341, 151, 109, 107.

Example 32

The procedure of Example 1 was repeated, except that 200 mg of 4-hydroxy-N-(4-hydroxyphenyl)benzamide was used in place of 2'-nitrobiphenyl-4-ol. The resulting crude product was crystallized from chloroform to obtain 242 mg of 4-[N-(4-sulfamoyloxyphenyl)carbamoyl]-phenyl sulfamate.

$^1$H-NMR(DMSO-d$_6$, δ): 7.26(2H, d, J=9 Hz), 7.42(2H, d, J=9 Hz), 7.83(2H, d, J=9 Hz), 7.96(2H, d, J=9 Hz), 8.10(4H, br s), 10.35(1H, br s).

HR-SIMS(m/z): 388.0270(MH$^+$).

Example 33

The procedure of Example 1 was repeated, except that 231 mg of N-ethyl-4-hydroxy-N-(4-hydroxyphenyl)benzamide was used in place of 2'-nitrobiphenyl-4-ol. The resulting crude product was purified by TLC (using a 9:1 mixture of chloroform and methanol as the developing solvent) to obtain 242 mg of 4-[N-ethyl-N-(4-sulfamoyloxyphenyl)-carbamoyl]phenyl sulfamate.

$^1$H-NMR(CDCl$_3$, δ): 1.23(3H, t, J=7 Hz), 3.94(2H, q, J=7 Hz), 6.9–7.4(8H, m).

MS(m/z): 415(M$^+$), 336, 119.

Example 34

The procedure of Example 1 was repeated, except that 200 mg of 4-hydroxy-N-(4-hydroxyphenyl)-N-methylbenzamide was used in place of 2'-nitrobiphenyl-4-ol. The resulting crude product was purified by TLC (using a 5:1 mixture of chloroform and methanol as the developing solvent) to obtain 200 mg of 4-[N-methyl-N-(4-sulfamoyloxyphenyl)-carbamoyl]phenyl sulfamate.

$^1$H-NMR(CDCl$_3$, δ): 3.48(3H, s), 6.9–7.4(8H, m).

ESI-MS(m/z): 402(MH$^+$).

Example 35

The procedure of Example 1 was repeated, except that 200 mg of 4-hydroxy-N-(3-hydroxyphenyl)benzamide was used in place of 2'-nitrobiphenyl-4-ol. The resulting crude product was purified by TLC (using a 5:1 mixture of chloroform and methanol as the developing solvent) to obtain 185 mg of 4-[N-(3-sulfamoyloxyphenyl)carbamoyl]-phenyl sulfamate.

$^1$H-NMR(DMSO-d$_6$, δ): 6.9–8.2(12H, m), 10.44(1H, br 8).

ESI-MS(m/z): 388(MH$^+$).

Example 36

The procedure of Example 1 was repeated, except that 222 mg of 4-hydroxy-N-(3-hydroxyphenyl)-N-methylbenzamide was used in place of 2'-nitrobiphenyl-4-ol. The resulting crude product was purified by TLC (using a 9:1 mixture of chloroform and methanol as the developing solvent) to obtain 188 mg of 4-[N-methyl-N-(3-sulfamoyloxyphenyl)-carbamoyl]phenyl sulfate.

$^1$H-NMR(CDCl$_3$, δ): 3.51(3H, s), 6.7–8.5(8H, m).

ESI-MS(m/z): 402(MH$^+$).

Example 37

The procedure of Example 2 was repeated, except that 83 mg of N'-acetyl-4-hydroxy-N-phenylbenzohydrazide was used in place of 2'-nitrobiphenyl-4-ol. The resulting crude product was crystallized from ethyl acetate to obtain 53 mg of 4-(N'-acetyl-N-phenylhydrazino-carbonyl)phenyl sulfamate.

$^1$H-NMR(CD$_3$OD, δ): 1.90(3H, s), 7.1–7.7(9H, m).
MS(m/z): 270, 200, 150, 121.

Example 38

The procedure of Example 2 was repeated, except that 568 mg of 4[-N-(4-hydroxybenzyl)-N-(1,2,4-triazol-4-yl)amino]benzonitrile was used in place of 2'-nitrobiphenyl-4-ol, and 30 ml of N,N-dimethylformamide was used in place of methylene chloride. The resulting crude product was purified by Silica gel column chromatography (using a 10:1 mixture of chloroform and methanol as the eluent) to obtain 512 mg of 4-[N-(4-cyano-phenyl)-N-(1,2,4-triazol-4-yl)aminomethyl]phenyl sulfamate.

$^1$H-NMR(DMSO-d$_6$, δ): 5.08(2H, s), 6.74(2H, d, J=9.2 Hz), 7.23(2H, d, J=8.8 Hz), 7.39(2H, d, J=8.8 Hz), 7.74(2H, d, J=9.0 Hz), 7.96(2H, br s), 8.80(2H, s).
MS(m/z): 291(M+—SO$_2$NH), 185.

Example 39

The procedure of Example 2 was repeated, except that 2.81 g of N-(4-cyanophenyl)-4-hydroxy-N-(1,2,4-triazol-4-yl)benzamide was used in place of 2'-nitrobiphenyl-4-ol, and 28 ml of N,N-dimethylformamide was used in place of methylene chloride. The resulting crude product was purified by silica gel column chromatography (using a 10:1 mixture of chloroform and methanol as the eluent) to obtain 1.07 g of 4-[N-(4-cyanophenyl)-N-(1,2,4-triazol-4-yl)carbamoyl]phenyl sulfamate.

$^1$H-NMR(DMSO-d$_6$, δ): 7.29(2H, d, J=8.8 Hz), 7.58(2H, d, J=8.8 Hz), 7.62 (2H, d, J=8.6 Hz), 7.90(2H, d, J=8.8 Hz), 8.13(2H, br s), 9.11 (2H, s).
MS(m/z): 384(M$^+$), 185.

Example 40

32 mg of 4-formylphenyl sulfamate was added to a mixture composed of 11.5 μl of aniline, 0.2 ml of ethanol, 27 mg of sodium acetate, 84 μl of acetic acid, and 0.25 ml of water, and dissolved therein by heating. The resulting mixture was cooled with ice, and 20 mg of sodium borohydride was slowly added thereto. After the reaction mixture was stirred at room temperature for 10 minutes, a saturated aqueous solution of sodium hydrogen carbonate was added thereto, and the product was extracted with ethyl acetate. After the organic layer was washed with water and dried over anhydrous sodium sulfate, the solvent was distilled off under reduced pressure. The resulting crude product was purified by TLC (using a 9:1 mixture of chloroform and methanol as the developing solvent) to obtain 27 mg of 4-N-phenylaminomethyl)phenyl sulfamate.

$^1$H-NMR(CDCl$_3$, δ): 4.32(2H, s), 5.0(2H, br), 6.5–7.5 (10H, m).
MS(m/z): 278(M$^+$), 199.

Example 41

The procedure of Example 40 was repeated, except that 15 mg of 4-aminobenzonitrile was used in place of aniline. Thus, there was obtained 16 mg of 4-[N-(4-cyanophenyl)aminomethyl]phenyl sulfamate.

$^1$H-NMR(CDCl$_3$, δ): 4.37(2H, s), 6.1(1H, br), 6.58(2H, d, J=8.8 Hz), 7.2–7.5(6H, m).
MS(m/z): 303(M$^+$), 224.

Example 42

The procedure of Example 40 was repeated, except that 15 mg of 2-aminobenzonitrile was used in place of aniline. Thus, there was obtained 5 mg of 4-[N-(2-cyanophenyl)aminomethyl]phenyl sulfamate.

$^1$H-NMR(CDCl$_3$, δ): 4.44(2H, d, J=5.7 Hz), 5.0(3H, br), 6.60(1H, br d, J=7.7 Hz), 6.74(1H, dd, J=1.0, 7.7 Hz), 7.0–8.0(6H, m).
MS(m/z): 303(M$^+$), 224.

Example 43

The procedure of Example 40 was repeated, except that 27.5 mg of 4-aminophenol was used in place of aniline. Thus, there was obtained 27 mg of 4-[N-(4-hydroxyphenyl)aminomethyl]phenyl sulfamate.

$^1$H-NMR(CDCl$_3$, δ): 4.24(2H, s), 6.4–7.5(8H, m).
MS(m/z): 294(M$^+$), 215.

Example 44

The procedure of Example 40 was repeated, except that 34.8 mg of 4-nitroaniline was used in place of aniline. Thus, there was obtained 7 mg of 4-[N-(4-nitrophenyl)aminomethyl]phenyl sulfamate.

$^1$H-NMR(CDCl$_3$, δ): 4.43(2H, s), 6.56(2H, d, J=9.2 Hz), 7.31(4H, s), 8.05(2H, d, J=9.2 Hz).
MS(m/z): 323(M$^+$), 244.

Example 45

The procedure of Example 2 was repeated, except that 66 mg of 4-[N-(4-hydroxybenzyl)-N-(4-methoxyphenyl)amino]benzonitrile was used in place of 2'-nitrobiphenyl-4-ol, and 2.9 ml of N,N-dimethylformamide was used in place of methylene chloride. Thus, there was obtained 47 mg of 4-[N-(4-cyanophenyl)-N-(4-methoxyphenyl)aminomethyl]phenyl sulfamate.

$^1$H-NMR(CDCl$_3$, δ): 3.82(3H, s), 4.8–5.1(4H, m), 6.5–7.5(12H, m).
MS(m/z): 409(M$^+$), 330.

Example 46

The procedure of Example 2 was repeated, except that 60 mg of 4-[N-(4-hydroxybenzyl)-N-phenylamino]benzonitrile was used in place of 2'-nitrobiphenyl-4-ol, and 2.9 ml of N,N-dimethylformamide was used in place of methylene chloride. Thus, there was obtained 51 mg of 4-[N-(4-cyanophenyl)-N-phenylaminomethyl]phenyl sulfamate.

$^1$H-NMR(CDCl$_3$, δ): 4.8–5.1(4H, m), 6.5–7.5(13H, m).
MS(m/z): 379(M$^+$), 300.

Example 47

The procedure of Example 2 was repeated, except that 33 mg of N-(4-hydroxybenzyl)-4,4'-iminobisbenzonitrile was used in place of 2'-nitrobiphenyl-4-ol, and 1.45 ml of N,N-dimethylformamide was used in place of methylene chloride. Thus, there was obtained 18 mg of 4-[N,N-bis(4-cyanophenyl)aminomethyl]phenyl sulfamate.

$^1$H-NMR(CDCl$_3$, δ): 4.9–5.2(4H, m), 7.14(4H, d, J=9 Hz), 7.28(4H, s), 7.54(4H, d, J=8.8 Hz).

MS(m/z): 404(M$^+$), 325.

Example 48

The procedure of Example 2 was repeated, except that 11 mg of 4-[N-(4-hydroxybenzyl)-N-(4-pyridyl)amino] benzonitrile was used in place of 2'-nitrobiphenyl-4-ol. The resulting crude product was purified by TLC (using a 9:1 mixture of chloroform and methanol as the developing solvent) to obtain 5 mg of 4-[N-(4-cyanophenyl)-N-(4-pyridyl)aminomethyl]phenyl sulfamate.

$^1$H-NMR(CDCl$_3$, δ): 5.06(2H, s), 6.83(2H, dd, J=1.5, 5.1 Hz), 7.28 (4H, s), 7.32(2H, d, J=8.1 Hz), 7.66(2H, d, J=8.8 Hz), 8.26(2H, dd, J=1.3, 5.1 Hz).

MS(m/z): 301(M$^+$—SO$_2$NH), 195.

Example 49

The procedure of Example 2 was repeated, except that 50 mg of 4-N-phenylaminomethyl)phenol was used in place of 2'-nitrobiphenyl-4-ol. The resulting crude product was purified by TLC (using a 9:1 mixture of chloroform and methanol as the developing solvent) to obtain 21 mg of 4-(N-phenyl-N-sulfamoylaminomethyl)phenyl sulfamate.

$^1$H-NMR(CDCl$_3$+CD$_3$OD, δ): 4.79(2H, s), 7.2–7.4(9H, m).

MS(m/z): 357(M$^+$), 278.

Example 50

The procedure of Example 2 was repeated, except that 56 mg of 4-[N-(4-hydroxybenzyl)amino]benzonitrile was used in place of 2'-nitrobiphenyl-4-ol. The resulting crude product was purified by TLC (using a 9:1 mixture of chloroform and methanol as the developing solvent) to obtain 18 mg of 4-[N-(4-cyanophenyl)-N-sulfamoylaminomethyl]phenyl sulfamate.

$^1$H-NMR(CDCl$_3$, δ): 2.86(4H, s), 4.37(2H, s), 6.58(2H, d, J=8.8 Hz), 7.2–7.5(6H, m).

MS(m/z): 303(M$^+$—SO$_2$NH), 224.

Example 51

The procedure of Example 1 was repeated, except that 83 mg of N-(4-cyanophenyl)-N-(4-hydroxybenzyl) nicotinamide was used in place of 2'-nitrobiphenyl-4-ol. The resulting crude product was purified by TLC (using a 9:1 mixture of chloroform and acetone as the developing solvent) to obtain 19 mg of 4-[N-(4-cyanophenyl)-N-nicotinoylaminomethyl]phenyl sulfamate.

$^1$H-NMR(DMSO-d$_6$, δ): 5.19(2H, s), 7.1–7.5(7H, m), 7.6–7.8(3H, m), 7.93(2H, br s), 8.4–8.6(2H, m).

MS(m/z): 329 (M$^+$—SO$_2$NH), 223.

Example 52

The procedure of Example 2 was repeated, except that 78 mg of N-(4-cyanophenyl)-N-(4-hydroxyhenzyl)benzamide was used in place of 2'-nitrobiphenyl-4-ol. The resulting crude product was purified by TLC (using a 19:1 mixture of chloroform and acetone as the developing solvent) to obtain 45 mg of 4-[N-benzoyl-N-(4-cyanophenyl)aminomethyl]phenyl sulfamate.

$^1$H-NMR(DMSO-d$_6$, δ): 4.93(2H, s), 7.1–7.9(13H, m), 8.0–8.2(2H, m).

MS(m/z): 328(M$^+$—SO$_2$NH), 223.

Example 53

The procedure of Example 2 was repeated, except that 89 mg of 4-cyano-N-(4-cyanophenyl)-N-(4-hydroxybenzyl) benzamide was used in place of 2'-nitrobiphenyl-4-ol. The resulting crude product was purified by TLC (using a 19:1 mixture of chloroform and acetone as the developing solvent) to obtain 16 mg of 4-[N-(4-cyanobenzoyl)-N-(4-cyanophenyl)aminomethyl]phenyl sulfamate.

$^1$H-NMR(DMSO-d$_6$, δ): 4.94(2H, s), 7.1–7.8(10H, m), 8.07(2H, d, J=8.6 Hz), 8.22(2H, d, J=8.4 Hz).

MS(m/z): 353(M$^+$—SO$_2$NH), 236.

Example 54

The procedure of Example 1 was repeated, except that 73 mg of 4-hydroxy-N,N-diphenylbenzamide was used in place of 2'-nitrobiphenyl-4-ol. The resulting crude product was purified by TLC (using a 19:1 mixture of chloroform and methanol as the developing solvent) to obtain 50 mg of 4-(N,N-diphenylcarbamoyl)phenyl sulfamate.

$^1$H-NMR(DMSO-d$_6$, δ): 7.0–7.6(14H, m), 8.04(2H, br s).

MS(m/z): 368(M$^+$), 289.

Example 55

The procedure of Example 2 was repeated, except that 534 mg of N-benzyl-4-hydroxybenzamide was used in place of 2'-nitrobiphenyl-4-ol. The resulting crude product was purified by silica gel column chromatography (using a 10:1 mixture of chloroform and methanol as the eluent) to obtain 204 mg of 4-(N-benzylcarbamoyl)phenyl sulfamate.

$^1$H-NMR(CDCl$_3$, δ): 4.61(2H, d, J=5.7 Hz), 7.0–7.5(10H, m), 7.81(2H, d, J=8.6 Hz).

MS(m/z): 306(M$^+$), 227.

Example 56

The procedure of Example 1 was repeated, except that 54 mg of 4-hydroxy-N-phenylbenzamide was used in place of 2'-nitrobiphenyl-4-ol. The resulting crude product was purified by TLC (using a 10:1 mixture of chloroform and methanol as the developing solvent) to obtain 40 mg of 4-(N-phenylcarbamoyl)phenyl sulfamate.

$^1$H-NMR(DMSO-d$_6$, δ): 7.0–7.5(5H, m), 7.76(2H, d, J=7.9 Hz), 7.9–8.2(4H, m), 10.26(1H, br s).

MS(m/z): 292(M$^+$), 213.

Example 57

The procedure of Example 2 was repeated, except that 45 mg of 4-cyano-N-(4-hydroxybenzyl)-N-methylbenzamide was used in place of 2'-nitrobiphenyl-4-ol, and 1.5 ml of N,N-dimethylformamide was used in place of methylene chloride. The resulting crude product was purified by TLC (using a 4:1 mixture of chloroform and acetone as the developing solvent) to obtain 5 mg of 4-[N-(4-cyanobenzoyl)-N-methylaminomethyl]-phenyl sulfamate.

$^1$H-NMR(CDCl$_3$, δ): 2.73–3.20(3H, m), 4.3–4.8 (2H, br), 5.30(2H, s), 7.0–7.4(4H, m), 7.53(2H, d, J=8.4 Hz), 7.71 (2H, d, J=8.3 Hz).

MS(m/z): 345(M$^+$), 266.

Example 58

The procedure of Example 40 was repeated, except that 32 mg of 4-amino-1,2,4-triazole was used in place of aniline. The resulting crude product was purified by TLC (using a 4:1 mixture of chloroform and methanol as the developing solvent) to obtain 39 mg of 4-[N-(1,2,4-triazol-4-yl) aminomethyl]phenyl sulfamate.

$^1$H-NMR(CD$_3$OD, δ):4.10(2H, s), 6.71(2H, d, J=8.6 Hz), 7.06(2H, d, J=8.6 Hz), 8.27(2H, s).

Example 59

The procedure of Example 2 was repeated, except that 26 mg of 3-cyano-N-(4-hydroxybenzyl)-N-(1,2,4-triazol-4-yl) benzamide was used in place of 2'-nitrobiphenyl-4-ol, and 0.5 ml of N,N-dimethylformamide was used in place of methylene chloride. The resulting crude product was purified by TLC (using a 7:1 mixture of chloroform and methanol as the developing solvent) to obtain 10 mg of 4-[N-(3cyanobenzoyl)-N-(1,2,4-triazol-4-yl)aminomethyl]phenyl sulfamate.

$^1$H-NMR(DMSO-d$_6$, δ): 5.60(2H, s), 7.16–8.06(8H, m), 8.16–8.27 (2H, m), 9.24(1H, s), 10.90(1H, s).

MS(m/z): 399(MH$^+$).

Example 60

The procedure of Example 2 was repeated, except that 71 mg of 4-[N-(4-hydroxybenzyl)-N-(3-pyridyl)amino] benzonitrile was used in place of 2'-nitrobiphenyl-4-ol, and 1.8 ml of N,N-dimethylformamide was used in place of methylene chloride. The resulting crude product was purified by TLC (using a 19:1 mixture of chloroform and methanol as the developing solvent) to obtain 52 mg of 4-[N-(4-cyanophenyl)-N-(3-pyridyl)aminomethyl]phenyl sulfamate.

$^1$H-NMR(DMSO-d$_6$, δ): 5.12(2H, s), 6.87(2H, d, J=5.8 Hz), 7.12–7.97 (8H, m), 8.41(1H, dd, J=1.2, 3.0 Hz), 8.59 (1H, d, J=1.7 Hz).

MS(m/z): 301(M$^+$—SO$_2$NH).

Example 61

The procedure of Example 2 was repeated, except that 38 mg of 4-[N-(4-hydroxybenzyl)-N-methylamino]benzonitrile was used in place of 2'-nitrobiphenyl-4-ol, and 1.2 ml of N,N-dimethylformamide was used in place of methylene chloride. The resulting crude product was purified by TLC (using a 19:1 mixture of chloroform and methanol as the developing solvent) to obtain 19 mg of 4-[N-(4-cyanophenyl)-N-methyl-aminomethyl]phenyl sulfamate.

$^1$H-NMR(CD$_3$OD, δ): 3.15(3H, s), 4.67(2H, s), 6.80(2H, d, J=7.8 Hz), 7.26(4H, s), 7.44(2H, d, J=7.8 Hz).

MS(m/z): 317(M$^+$), 238(M$^+$—SO$_2$NH).

Example 62

The procedure of Example 2 was repeated, except that 24 mg of 4-[ethyl-N-(4-hydroxybenzyl)amino]benzonitrile was used in place of 2'-nitrobiphenyl-4-ol, and 0.7 ml of N,N-dimethylformamide was used in place of methylene chloride. The resulting crude product was purified by TLC (using a 19:1 mixture of chloroform and methanol as the developing solvent) to obtain 13 mg of 4-[N-(4-cyanophenyl)-N-ethyl-aminomethyl]phenyl sulfamate.

$^1$H-NMR(CD$_3$OD, δ): 1.23(3H; t, J=4.5 Hz), 3.59(2H, q, J=4.7 Hz), 4.64(2H,s), 6.76(2H, d, J=5.8 Hz), 7.25(4H, s), 7.40(2H, d, J=5.8 Hz).

MS(m/z): 331(M$^+$), 252 (M$^+$—SO$_2$NH).

Example 63

The procedure of Example 2 was repeated, except that 37 mg of N-(4-cyanophenyl)-N-(4-hydroxybenzyl)-2-thiophenecarboxamide was used in place of 2'-nitrobiphenyl-4-ol, and 0.9 ml of 1,2-dichloroethane was used in place of methylene chloride. The resulting crude product was purified by TLC (using a 19:1 mixture of chloroform and methanol as the developing solvent) to obtain 17 mg of 4-[N-(4-cyanophenyl)-N-(2-thienylcarbonyl)aminomethyl]phenyl sulfamate.

$^1$H-NMR(CD$_3$OD, δ): 5.05(2H, d, J=2.2 Hz), 5.22(2H, br s), 6.70–7.72 (11H, m).

MS(m/z): 413(M$^+$), 334(M$^+$—SO$_2$NH).

Example 64

The procedure of Example 2 was repeated, except that 43 mg of N-(4-cyanophenyl)-N-(4-hydroxybenzyl)-3-thiophenecarboxamide was used in place of 2'-nitrobiphenyl-4-ol, and 1.0 ml of 1,2-dichloroethane was used in place of methylene chloride. The resulting crude product was purified by TLC (using a 19:1 mixture of chloroform and methanol as the developing solvent) to obtain 23 mg of 4-[N-(4-cyanophenyl)-N-(3-thienylcarbonyl)aminomethyl]phenyl sulfamate.

$^1$H-NMR(CD$_3$OD, δ): 5.16(2H, s), 6.74–7.77(11H, m).

MS(m/z): 334(M$^+$—SO$_2$NH).

Example 65

The procedure of Example 2 was repeated, except that 83 mg of N-(4-cyanophenyl)-4-hydroxybenzamide was used in place of 2'-nitrobiphenyl-4-ol, and 2.6 ml of N,N-dimethylformamide was used in place of methylene chloride. The resulting crude product was purified by TLC (using a 13:1 mixture of chloroform and methanol as the developing solvent) to obtain 8 mg of 4-[N-(4-cyanophenyl) carbamoyl]phenyl sulfamate.

$^1$H-NMR(CD$_3$OD, δ): 6.87(2H, d, J=5.8 Hz), 7.56–8.00 (6H, m).

MS(m/z): 238(M$^+$—SO$_2$NH).

Example 66

The procedure of Example 2 was repeated, except that 279 mg of N-(4-cyanophenyl)-4-hydroxy-N-methylbenzamide was used in place of 2'-nitrobiphenyl-4-ol, and 8.4 ml of N,N-dimethylformamide was used in place of methylene chloride. The resulting crude product was purified by TLC (using a 13:1 mixture of chloroform and methanol as the developing solvent) to obtain 143 mg of 4-[-(4-cyanophenyl)-N-methyl-carbamoyl]phenyl sulfamate.

$^1$H-NMR(CD$_3$OD, δ): 3.50(3H, s), 7.08–7.49(6H, m), 7.63(2H, d, J=6.0 Hz).

MS(m/z): 331(M$^+$), 252(M$^+$—SO$_2$NH).

Example 67

The procedure of Example 2 was repeated, except that 24 mg of N'N'-dimethyl-4-hydroxybenzohydrazide was used in place of 2'-nitrobiphenyl-4-ol. The resulting crude product was purified by TLC (using a 7:1 mixture of chloroform and methanol as the developing solvent) to obtain 2 mg of 4-(N',N'-dimethylhydrazinocarbonyl)phenyl sulfamate.

$^1$H-NMR(CD$_3$OD, δ):2.65(6H, s), 7.39(2H, d, J=5.5 Hz), 7.83(2H, d, J=5.7 Hz).

MS(m/z): 259(M$^+$).

Example 68

The procedure of Example 2 was repeated, except that 23 mg of 2-hydroxy-N-(4-hydroxyphenyl)benzamide was used in place of 2'-nitrobiphenyl-4-ol, and 1.5 ml of N,N-dimethylformamide was used in place of methylene chloride. Thus, there was obtained 21 mg of 2-[N-(4-sulfamoyloxyphenyl)carbamoyl]phenyl sulfamate.

$^1$H-NMR(DMSO-d$_6$, δ): 6.7–8.4(12H, m), 10.49(1H, br s).

MS(m/z): 308(M$^+$—SO$_2$NH), 229.

Example 69

The procedure of Example 2 was repeated, except that 23 mg of 3-hydroxy-N-(2-hydroxyphenyl)benzamide was used in place of 2'-nitrobiphenyl-4-ol, and 1.5 ml of N,N-dimethylformamide was used in place of methylene chloride. Thus, there was obtained 26 mg of 3-[N-(2-sulfamoyloxyphenyl)carbamoyl]phenyl sulfamate.

$^1$H-NMR(DMSO-d$_6$, δ): 7.3–8.3(13H, m).

MS(m/z): 290(M$^+$—HOSO$_2$NH$_2$), 211.

Example 70

The procedure of Example 2 was repeated, except that 23 mg of 3-hydroxy-N-(3-hydroxyphenyl)benzamide was used in place of 2'-nitrobiphenyl-4-ol, 4-ol, and 1.5 ml of N,N-dimethylformamide was used in place of methylene chloride. Thus, there was obtained 25 mg of 3-[N-(3-sulfamoyloxyphenyl)carbamoyl]phenyl sulfamate.

$^1$H-NMR(DMSO-d$_6$, δ): 6.9–8.1(12H, m), 10.48(1H, br s).

MS(m/z): 290(M$^+$—HOSO$_2$NH$_2$).

Example 71

The procedure of Example 2 was repeated, except that 23 mg of 3-hydroxy-N-(4-hydroxyphenyl)benzamide was used in place of 2'-nitrobiphenyl-4-ol, and 1.5 ml of N,N-dimethylformamide was used in place of methylene chloride. Thus, there was obtained 33 mg of 3-[N-(4-sulfamoyloxyphenyl)carbamoyl]phenyl sulfamate.

$^1$H-NMR(DMSO-d$_6$, δ): 7.1–8.1(12H, m), 10.41(1H, br s).

MS(m/z): 290(M$^+$—HOSO$_2$NH$_2$), 229.

Example 72

The procedure of Example 2 was repeated, except that 23 mg of 4-hydroxy-N-(2-hydroxyphenyl)benzamide was used in place of 2'-nitrobiphenyl-4-ol, and 1.5 ml of N,N-dimethylformamide was used in place of methylene chloride. Thus, there was obtained 18 mg of 4-[N-(2-sulfamoyloxyphenyl)carbamoyl]phenyl sulfamate.

$^1$H-NMR(DMSO-d$_6$, δ): 7.3–8.5(12H, m).

MS(m/z): 290(M$^+$—HOSO$_2$NH$_2$), 211.

Example 73

The procedure of Example 2 was repeated, except that 271 mg of 4-[N-(4-hydroxybenzyl)-N-(2-pyrazinyl)amino]benzonitrile was used in place of 2'-nitrobiphenyl-4-ol. The resulting crude product was purified by TLC (using a 19:1 mixture of chloroform and methanol as the developing solvent) to obtain 211 mg of 4-[N-(4-cyanophenyl)-N-(2-pyrazinyl)aminomethyl]phenyl sulfamate.

$^1$H-NMR(DMSO-d$_6$, δ): 5.32(2H, s), 7.19(2H, d, J=5.5 Hz), 7.35(2H, d, J=6.0 Hz), 7.53(2H, d, J=6.0 Hz), 7.77(2H, d, J=5.5 Hz), 7.83–8.39 (3H, m).

MS(m/z): 302(M$^+$—SO$_2$NH).

Example 74

The procedure of Example 1 was repeated, except that 118 mg of 4-[N-(4-hydroxybenzyl)-N-(2-thenyl)amino]benzonitrile was used in place of 2'-nitrobiphenyl-4-ol. The resulting crude product was purified by TLC (using a 10:1 mixture of chloroform and tetrahydrofuran as the developing solvent) to obtain 4-[N-(4-cyanophenyl)-N-(2-thenyl)aminomethyl]phenyl sulfamate.

$^1$H-NMR(CD$_3$OD, δ): 4.75(2H, s), 4.89(2H, s), 6.73–7.54 (11H, m).

MS(m/z): 320(M$^+$—SO$_2$NH).

Example 75

The procedure of Example 1 was repeated, except that 88 mg of 4-[N-(4-hydroxybenzyl)-N-(3-thenyl)amino]benzonitrile was used in place of 2'-nitrobiphenyl-4-ol. The resulting crude product was purified by TLC (using a 10:1 mixture of chloroform and tetrahydrofuran as the developing solvent) to obtain 4-[N-(4-cyanophenyl)-N-(3-thenyl)aminomethyl]phenyl sulfamate.

$^1$H-NMR(CD$_3$OD, δ): 4.74(4H, s), 6.69–7.51(11H, m).

MS(m/z): 399(M$^+$), 320(M$^+$—SO$_2$NH).

Example 7

A mixture composed of 215 mg of 2'-nitrobiphenyl-4-ol and 1 ml of toluene was cooled with ice, and 148 mg of chlorosulfonyl isocyanate was added dropwise thereto, followed by refluxing for 17 hours. After water was added to the reaction mixture under cooling with ice, the product was extracted with ethyl acetate. The organic layer was washed with water and dried over anhydrous magnesium sulfate. After the solvent was distilled off, the resulting crude product was purified by TLC (using a 10:1 mixture of chloroform and methanol as the developing solvent) to obtain 160 mg of 2'-nitrobiphenyl-4-yl sulfamate.

Example 77

The procedure of Example 1 was repeated, except that 88 mg of 4-(1-naphthyl)phenol was used in place of 2'-nitrobiphenyl-4-ol. The resulting crude product was purified by TLC (using a 2:1 mixture of hexane and ethyl acetate as the developing solvent) to obtain 63 mg of 4-(1-naphthyl)phenyl sulfamate.

$^1$H-NMR(CDCl$_3$, δ): 4.99(2H, br s), 7.28–7.66(8H, m), 7.66–8.03 (3H, m).

MS(m/z): 299(M$^+$), 220.

Example 78

The procedure of Example 1 was repeated, except that 98 mg of 2-hydroxy-9-fluorenone was used in place of 2'-nitrobiphenyl-4-ol. Thus, there was obtained 55 mg of 9-oxofluoren-2-yl sulfamate.

$^1$H-NMR(CDCl$_3$, δ): 7.22–7.77(7H, m).

MS(m/z). 275(M$^+$), 196.

Example 79

The procedure of Example 1 was repeated, except that 36 mg of fluoren-2-ol was used in place of 2'-nitrobiphenyl-4-ol. The resulting crude product was purified by TLC (using a 1:1 mixture of diethyl ether and hexane as the developing solvent) to obtain 22 mg of fluoren-2-yl sulfamate.

$^1$H-NMR(CDCl$_3$, δ): 3.91(2H, s), 7.13–7.91(7H, m).

MS(m/z): 261(M$^+$), 181.

Example 80

The procedure of Example 1 was repeated, except that 33 mg of 4-(3-pyridyl)phenol was used in place of 2'-nitrobiphenyl-4ol. The resulting crude product was purified by TLC (using a 10:1 mixture of chloroform and methanol as the developing solvent) to obtain 4-(3-pyridyl)phenyl sulfamate.

$^1$H-NMR(CD$_3$OD, δ): 7.32–7.85(4H, m), 7.97–8.19 (1H, m), 8.53(1H, dd, J=1.2, 3.2 Hz), 8.80(1H, d, J=1.5 Hz).

MS(m/z): 250(M$^+$), 171.

Example 81

The procedure of Example 1 was repeated, except that 102 mg of 4-(2-methylthiazol-4-yl)phenol was used in place of 2'-nitrobiphenyl-4-ol. The resulting crude product was purified by TLC (using a 10:1 mixture of chloroform and methanol as the developing solvent) to obtain 14 mg of 4-(2-methylthiazol-4-yl)phenyl sulfamate.

$^1$H-NMR(CDCl$_3$, δ): 2.77(3H, s), 7.31(1H, s), 7.35(2H, d, J=6 Hz), 7.85(2H, d, J=5.7 Hz).

MS(m/z): 270(M$^+$), 190.

Example 82

The procedure of Example 1 was repeated, except that 52 mg of 4-(2-aminothiazol-4-yl)phenol was used in place of 2'-nitrobiphenyl-4-ol. The resulting crude product was purified by TLC (using a 10:1 mixture of chloroform and methanol as the developing solvent) to obtain 8 mg of 4-(2-sulfamoylaminothiazol-4-yl)phenyl sulfamate.

$^1$H-NMR(CDCl$_3$, δ): 6.96(1H, s), 7.30(2H, d, J=5.7 Hz), 7.86(2H, d, J=5.7 Hz), 8.21(1H, s).

MS(m/z): 350(M$^+$), 270, 192.

Example 83

The procedure of Example 1 was repeated, except that 23 mg of 5-(4-hydroxyphenyl)-N-methyl-3-isoxazolecarboxamide was used in place of 2'-nitrobiphenyl-4-ol. The resulting crude product was purified by TLC (using a 10:1 mixture of chloroform and methanol as the developing solvent) to obtain 8 mg of 4-[3-(N-methylcarbamoyl)isoxazol-5-yl]phenyl sulfamate.

$^1$H-NMR(CD$_3$OD, δ): 2.94(3H, s), 7.07(1H, s), 7.48(2H, d, J=5.7 Hz), 7.93(2H, d, J=5.7 Hz).

MS(m/z): 297(M$^+$), 218.

Example 84

The procedure of Example 1 was repeated, except that 102 mg of 3-chlorobiphenyl-4-ol was used in place of 2'-nitrobiphenyl-4-ol. The resulting crude product was purified by TLC (using a 2:1 mixture of hexane and ethyl acetate as the developing solvent) to obtain 68 mg of 3-chlorobiphenyl-4-yl sulfamate.

$^1$H-NMR(CDCl$_3$, δ): 5.07(2H, br s), 7.30–7.76(8H, m).

MS(m/z): 285(M$^+$+2), 283(M$^+$), 206, 204.

Example 85

The procedure of Example 1 was repeated, except that 25 mg of 3-bromobiphenyl-4-ol was used in place of 2'-nitrobiphenyl-4-ol. The resulting crude product was purified by TLC (using a 1:1 mixture of diethyl ether and hexane as the developing solvent) to obtain 17 mg of 3-bromobiphenyl-4-yl sulfamate.

$^1$H-NMR(CDCl$_3$, δ): 7.30–7.80(8H, m).

MS(m/z): 329(M$^+$+2), 327(M$^+$), 249.

Example 86

The procedure of Example 1 was repeated, except that 30 mg of 3-iodobiphenyl-4-ol was used in place of 2'-nitrobiphenyl-4-ol. The resulting crude product was purified by TLC (using a 1:1 mixture of diethyl ether and hexane as the developing solvent) to obtain 10 mg of 3-iodobiphenyl-4-yl sulfamate.

$^1$H-NMR(CDCl$_3$, δ): 5.12(2H, br s), 7.30–7.70(8H, m).

MS(m/z): 375(M$^+$), 296.

Example 87

The procedure of Example 1 was repeated, except that 228 mg of N-(4-hydroxybiphenyl-3-yl)acetamide was used in place of 2'-nitrobiphenyl-4-ol. Thus, there was obtained 92 mg of 3-(N-acetyl)amino-biphenyl-3-yl sulfamate.

$^1$H-NMR(CDCl$_3$, δ): 2.22(3H, s), 7.31–7.67(8H, m), 8.40 (1H, br s).

MS(m/z): 306(M$^+$), 227, 185.

Example 88

20 mg of N-(4'-hydroxybiphenyl-4-yl)methanesulfonamide was dissolved in 0.2 ml of N,N-dimethyformamide, and 11 μl of triethylamine was added thereto under cooling with ice, followed by stirring for 30 minutes under cooling with ice. 35 mg of sulfamoyl chloride was added to this mixture, followed by stirring at room temperature for 3 hours. After the reaction mixture was poured into a saturated aqueous solution of sodium chloride, the product was extracted with ethyl acetate. The organic layer was washed with water and dried over anhydrous magnesium sulfate. After the solvent was distilled off, the resulting crude product was purified by TLC (using a 1:1 mixture of acetone and hexane as the developing solvent) to obtain 23 mg of 4'-(N-methyl-sulfonyl)aminobiphenyl-4-yl sulfamate.

$^1$H-NMR(DMSO-d$_6$, δ): 3.01(3H, s), 7.30(2H, d, J=7.8 Hz), 7.34(2H, d, J=7.8 Hz), 7.63(2H, d, J=7.8 Hz), 7.69(2H, d, J=7.8 Hz), 7.98(2H, s), 9.83(1H, s).

MS(m/z): 342(M$^+$), 184.

Example 89

The procedure of Example 88 was repeated, except that 105 mg of N-(4'-hydroxybiphenyl-2-yl)methanesulfonamide was used in place of N-(4'-hydroxybiphenyl-4-yl)methanesulfonamide. The resulting crude product was purified by TLC (using a 6:1 mixture of chloroform and acetone as the developing solvent) to obtain 111 mg of 2'-(N-methyl-sulfonyl)aminobiphenyl-4-yl sulfamate.

$^1$H-NMR(DMSO-d$_6$, δ): 2.74(3H, s), 7.34(2H, d, J=8.6 Hz), 7.3–7.5(4H, m),7.53(2H, d, J=8.6 Hz), 8.03(2H, 8), 8.95(1H, s).

MS(m/z): 342(M$^+$), 263, 184.

Example 90

The procedure of Example 88 was repeated, except that 129 mg of 4'-hydroxybiphenyl-4-yl methanesulfonate was used in place of N-(4'-hydroxybiphenyl-4-yl)methanesulfonamide. The resulting crude product was purified by TLC (using a 1:1 mixture of acetone and hexane as the developing solvent) to obtain 133 mg of 4'-methylsulfonyloxy-biphenyl-4-yl sulfamate.

$^1$H-NMR(DMSO d$_6$, δ): 3.40(3H, s), 7.3–7.4(2H, m), 7.4–7.5(2H, m), 7.7–7.8(4H, m), 8.01(2H, s).

MS(m/z): 343(M$^+$), 264, 185.

Example 91

The procedure of Example 2 was repeated, except that 100 mg of (2Z)-3-(4-hydroxyphenyl)-2-phenylprop-2-

Example 92

The procedure of Example 2 was repeated, except that 122 mg of (2Z)-2,3-bis(4-hydroxyphenyl)prop-2-enenitrile was used in place of 2'-nitrobiphenyl-4-ol, and 1,2-dichloroethane was used in place of methylene chloride. The resulting crude product was purified by TLC (using a 3:1 mixture of chloroform and acetone as the developing solvent) to obtain 86 mg of 4-[(1Z)-2-(4-sulfamoyloxyphenyl)-1-cyanovinyl]phenyl sulfamate.

$^1$H-NMR(CD$_3$OD, δ): 7.46(2H, d, J=8.5 Hz), 7.49(2H, d, J=8.5 Hz), 7.7–7.9(3H, m), 8.02(2H, d, J=9.0 Hz).

MS(m/z): 316(M$^+$−79), 237.

Example 93

The procedure of Example 2 was repeated, except that 100 mg of (2Z)-2-(4-hydroxybenzyl)-3-phenylprop-2-enenitrile was used in place of 2'-nitrobiphenyl-4-ol, and 1,25-dichloroethane was used in place of methylene chloride. The resulting crude product was purified by TLC (using a 15:1 mixture of chloroform and methanol as the developing solvent) to obtain 104 mg of 4-[(1Z)-1-cyano-2-phenylvinyl]phenyl sulfamate.

$^1$H-NMR(CD$_3$OD, δ): 7.3–7.6(5H, m), 7.6–8.1(5H, m).

MS(m/z): 300(M$^+$), 221.

Example 94

The procedure of Example 2 was repeated, except that 81 mg of 4-[N-(4-hydroxybenzyl)-N-(2-pyrimidyl)amino]benzonitrile was used in place of 2'-nitrobiphenyl-4-ol, and N,N-dimethylformamide was used in place of methylene chloride. The resulting crude product was purified by TLC (using a 10:1 mixture of chloroform and methanol as the developing solvent) to obtain 22 mg of 4[-N-(4-cyanophenyl)-N-(2-pyrimidyl)aminomethyl]phenyl sulfamate.

$^1$H-NMR(DMSO-d$_6$, δ): 5.27(2H, br s), 7.27(4H, d, J=3.8 Hz), 7.4–7.8 (2H, m), 7.8–8.1(3H, m), 8.2–8.8(2H, m).

MS(m/z): 302(M$^+$−79), 195, 107.

Example 95

The procedure of Example 88 was repeated, except that 120 mg of 4'-hydroxy-4-nitro-2-biphenylcarbonitrile was used in place of N-(4'-hydroxybiphenyl-4-yl)methanesulfonamide, and 0.430 ml of N,N-dimethylsulfamoyl chloride was used in place of sulfamoyl chloride. The resulting crude product was purified by TLC (using a 16:1 mixture of chloroform and acetone as the developing solvent) to obtain 97 mg of 2'-cyano-4'-nitrobiphenyl-4-yl N,N-dimethylsulfamate.

$^1$H-NMR(DMSO-d$_6$, δ): 2.97(6H, s), 7.5–7.6(2H, m), 7.7–7.8(2H, m), 7.94(1H, d, J=8.8 Hz), 8.57(1H, dd, J=2.2, 8.3 Hz), 8.84(1H, d, J=2.2 Hz).

MS(m/z): 347(M$^+$), 240, 108.

Example 96

43 mg of 4'-aminobiphenyl-4-ol was dissolved in 0.7 ml of N,N-dimethylacetamide, and 107 mg of sulfamoyl chloride was added thereto under cooling with ice, followed by stirring at room temperature for 2.4 hours. After the reaction mixture was poured into a saturated aqueous solution of sodium chloride, the product was extracted with ethyl acetate. The organic layer was washed with water and dried over anhydrous magnesium sulfate. After the solvent was distilled off, the resulting crude product was purified by TLC (using a 17:10 mixture of chloroform and tetrahydrofuran as the developing solvent) to obtain 42 mg of 4'-(sulfamoylamino)biphenyl-4-yl sulfamate.

$^1$H-NMR(CD$_3$OD, δ): 7.30(2H, d, J=8.7 Hz), 7.37(2H, d, J=8.7 Hz), 7.56(2H, d, J=8.7 Hz), 7.63(2H, d, J=8.7 Hz).

MS(m/z): 343(M$^+$), 264, 184.

Example 97

The procedure of Example 96 was repeated, except that 75 mg of 2'-aminobiphenyl-4-ol was used in place of 4'-aminobiphenyl-4-ol. The resulting crude product was purified by TLC (using a 17:10 mixture of chloroform and tetrahydrofuran as the developing solvent) to obtain 36 mg of 2'-(sulfamoylamino)biphenyl-4-yl sulfamate.

$^1$H-NMR(CD$_3$OD, δ): 7.1–7.5(3H, m), 7.41(2H, d, J=8.6 Hz), 7.51(2H, d, J=8.6 Hz), 7.66(1H, dd, J=0.8, 7.9 Hz).

MS(m/z): 343(M$^+$), 264, 184.

Example 98

The procedure of Example 96 was repeated, except that 12 mg of (2Z)-2-[4-(N-sulfamoylamino)phenyl]-3-(4-hydroxyphenyl)prop-2-ene-nitrile was used in place of 4'-aminobiphenyl-4-ol. The resulting crude product was purified by TLC (using a 2:1 mixture of chloroform and acetone as the developing solvent) to obtain 5 mg of 4-{(1Z)-2-[4-(N-sulfamoylamino)phenyl]-2-cyanovinyl}phenyl sulfamate.

$^1$H-NMR(CD$_6$OD, δ): 7.16(2H, d, J=8.6 Hz), 7.31(2H, d, J=8.6 Hz), 7.67(2H, d, J=8.6 Hz), 7.74(1H, s), 7.97(2H, d, J=8.6 Hz).

MS(m/z): 315(M$^+$−79), 236.

Example 99

The procedure of Example 96 was repeated, except that 279 mg of methyl 4-[(1Z)-2-cyano-2-(4-hydroxyphenyl)vinyl]phenylcarboxylate was used in place of 4'-aminobiphenyl-4-ol. The resulting crude product was purified by TLC (using a 8:1 mixture of chloroform and tetrahydrofuran as the developing solvent) to obtain 284 mg of methyl 4-[(1Z)-2-(4-sulfamoyloxyphenyl)-2-cyanovinyl]phenylcarboxylate.

$^1$H-NMR(DMSO-d$_6$, δ): 3.89(3H, s), 7.44(2H, d, J=8.8 Hz), 7.88(2H, d, J=8.8 Hz), 8.05(2H, d, J=8.4 Hz), 8.1(4H, m), 8.14(1H, s).

MS(m/z): 358(M$^+$), 279, 248.

Example 100

262 mg of 2'-cyano-4'-nitrobiphenyl-4-yl sulfamate was dissolved in 2.5 ml of formic acid, and 445 mg of 10% palladium-carbon was added thereto, followed by stirring at room temperature for 5 minutes. After the reaction mixture was filtered to remove any insoluble matter and the filtrate was poured into a saturated aqueous solution of sodium chloride, the product was extracted with ethyl acetate. The organic layer was washed with water and dried over anhydrous magnesium sulfate. After the solvent was distilled off, the resulting crude product was purified by TLC (using a 10:1 mixture of chloroform and methanol as the developing solvent) to obtain 52 mg of 4'-amino-2'-cyanobiphenyl-4-yl sulfamate.

$^1$H-NMR(DMSO-d$_6$, δ): 5.73(2H, br s), 6.93(1H, dd, J=2.4, 8.4 Hz), 6.98(1H, d, J=2.4 Hz), 7.27(1H, d, J=8.4 Hz), 7.36(2H, d, J=8.4 Hz), 7.55(2H, d, J=8.4 Hz), 8.10(2H, s).

MS(m/z): 289(M$^+$), 210.

Example 101

The procedure of Example 100 was repeated, except that 101 mg of 4'-cyano-2'-nitrobiphenyl-4-yl sulfamate was used in place of 2'-cyano-4'-nitrobiphenyl-4-yl sulfamate. The resulting crude product was purified by TLC (using a 9:1 mixture of chloroform and methanol as the developing solvent) to obtain 15 mg of 2'-amino-4'-cyanobiphenyl-4-yl sulfamate.

$^1$H-NMR(CD$_3$OD, δ): 7.01(1H, dd, J=1.5, 7.7 Hz), 7.08 (1H, d, J=1.5 Hz), 7.15(1H, d, J=7.7 Hz), 7.43(2H, d, J=8.7 Hz), 7.48(2H, d, J=8.7 Hz).

MS(m/z): 289(M$^+$), 210.

Preparation Example 1

A mixture composed of 392 mg of 2-bromophenylacetonitrile, 334 mg of 4-methoxyphenylboronic acid, 0.9 mg of palladium acetate, 691 mg of potassium acetate, 645 mg of tetrabutylammonium bromide, and 2.2 ml of distilled water was stirred at 70° C. for 2 hours under an atmosphere of nitrogen. After the reaction mixture was poured into a saturated aqueous solution of sodium chloride, the product was extracted with ethyl acetate The organic layer was washed with water and dried over anhydrous magnesium sulfate. After the solvent was distilled off, the resulting crude product was purified by silica gel column chromatography (using a 3:1 mixture of hexane and ethyl acetate as the eluent) to obtain 343 mg of 4'-methoxy-2-biphenylaceto-nitrile.

$^1$H-NMR(CDCl$_3$, δ): 3.62(2H, s), 3.86(3H, s), 6.86–7.70 (8H, m).

MS(m/z): 223(M$^+$).

Preparation Example 2

89 mg of 4'-methoxy-2-biphenylacetonitrile was dissolved in 0.66 ml of methylene chloride, and 0.8 ml of a 1 M solution of boron tribromide in methylene chloride was added thereto under cooling with ice, followed by stirring for 40 minutes. This mixture was returned to room temperature and stirred for an additional 40 minutes. After the reaction mixture was poured into a saturated aqueous solution of sodium chloride, the product was extracted with ethyl acetate. The organic layer was washed with water and dried over anhydrous magnesium sulfate. After the solvent was distilled off, the resulting crude product was purified by TLC (using a 2:1 mixture of hexane and ethyl acetate as the developing solvent) to obtain 43 mg of 4'-hydroxy-2-biphenylacetonitrile.

$^1$H-NMR(CDCl$_3$, δ): 3.62(2H, s), 6.73–7.64(8H, m).

MS(m/z): 209(M$^+$).

Preparation Example 3

The procedure of Preparation Example 1 was repeated, except that 365 mg of 2-chloro-5-nitrobenzonitrile was used in place of 2-bromophenylacetonitrile. The resulting crude product was purified by silica gel column chromatography (using a 2:1 mixture of chloroform and hexane as the eluent) to obtain 428 mg of 4'-methoxy-4-nitro-2-biphenylcarbonitrile.

$^1$H-NMR(CDCl$_3$, δ): 3.89(3H, s), 7.07(2H, d, J=5.5 Hz), 7.55(2H, d, J=5.8 Hz), 7.67(1H, d, J=6.0 Hz), 8.43(1H, dd, J=1.7, 5.5 Hz), 8.60(1H, d, J=1.5 Hz).

MS(m/z): 254(M$^+$).

Preparation Example 4

The procedure of Preparation Example 2 was repeated, except that 102 mg of 4'-methoxy-4-nitro-2-biphenylcarbonitrile was used in place of 4'-methoxy-2-biphenylacetonitrile. The resulting crude product was purified by TLC (using a 3:1 mixture of hexane and ethyl acetate as the developing solvent) to obtain 87 mg of 4'-hydroxy-4-nitro-2-biphenylcarbonitrile.

$^1$H-NMR(CDCl$_3$, δ):6.99(2H, d, J=5.8 Hz), 7.49(2H, d, J=5.3 Hz), 7.68(1H, d, J=5.8 Hz), 8.44(1H, dd, J=1.7, 5.3 Hz), 8.60(1H, d, J=1.5 Hz).

MS(m/z): 240(M$^+$).

Preparation Example 5

The procedure of Preparation Example 1 was repeated, except that 548 mg of 4-chloro-3-nitrobenzonitrile was used in place of 2-bromophenylacetonitrile. The resulting crude product was purified by silica gel column chromatography (using a 2:1 mixture of chloroform and hexane as the eluent) to obtain 640 mg of 4'-methoxy-2-nitro-4-biphenylcarbonitrile.

$^1$H-NMR(CDCl$_3$, δ): 3.86(3H, s), 6.98(2H, d, J=5.7 Hz), 7.24(2H, d, J=5.7 Hz), 7.58(1H, d, J=5.3 Hz), 7.83(1H, dd, J=1.2, 5.3 Hz), 8.06(1H, d, J=1.2 Hz).

MS(m/z): 254(M$^+$).

Preparation Example 6

The procedure of Preparation Example 2 was repeated, except that 208 mg of 4'-methoxy-2-nitro-4-biphenylcarbonitrile was used in place of 4'-methoxy-2-biphenylacetonitrile. The resulting crude product was purified by TLC (using a 3:1 mixture of hexane and ethyl acetate as the developing solvent) to obtain 140 mg of 4'-hydroxy-2-nitro-4-biphenylcarbonitrile.

$^1$H-NMR(CDCl$_3$, δ): 6.91(2H, d, J=6.0 Hz), 7.16(2H, d, J=5.3 Hz), 7.59(1H, d, J=5.3 Hz), 7.85(1H, dd, J=0.8, 5.3 Hz), 8.07(1H, d, J=0.8 Hz).

MS(m/z): 240(M$^+$).

Preparation Example 7

A mixture composed of 15 g of 4-benzyloxybenzyl chloride and 15 g of 4-aminophenol was refluxed in 200 ml of N,N-dimethylformamide for 30 minutes. After water was added to the reaction mixture, the product was extracted with ethylacetate. The organic layer was washed with water and dried over anhydrous sodium sulfate. After the solvent was distilled off, the resulting crude product was purified by silica gel column chromatography (using a 50:1 mixture of chloroform and acetone as the eluent) to obtain 11 g of 4[-N-(4-benzyloxybenzyl)-amino]phenol.

$^1$H-NMR(CDCl$_3$, δ): 4.19(2H, s), 5.05(3H, s), 6.4–7.5 (13H, m).

MS(m/z): 305(M$^+$), 197, 91.

Preparation Example 8

500 mg of 4-[N-(4-benzyloxybenzyl)amino]phenol was dissolved in 4 ml of pyridine, and 1 ml of methanesulfonyl chloride was added thereto under cooling with ice, followed by stirring for 30 minutes. After water was added to the reaction mixture, the precipitated crystals were separated by filtration to obtain 719 mg of 4-[N-(4-benzyloxybenzyl)-N-methylsulfonylamino]phenyl methanesulfonate.

$^1$H-NMR(CDCl$_3$, δ): 2.93(3H, s), 3.13(3H, s), 4.77(2H, s), 5.02(2H, s), 6.7–7.5 (13H, m).

MS(m/z): 197, 91.

Preparation Example 9

A mixture composed of 350 mg of 4-[N-(4-benzyloxybenzyl)-N-methylsulfonylamino]phenyl methanesulfonate, 350 mg of 10% palladium-carbon, and 10 ml of dioxane was stirred for 2 days under an atmospheric pressure of hydrogen. The reaction mixture was filtered to remove any insoluble matter, and the solvent was distilled off from the filtrate. Thus, there was obtained 260 mg of 4-[N-(4-hydroxybenzyl)-N-methylsulfonylamino]phenyl methanesulfonate.

$^1$H-NMR(CDCl$_3$, δ): 2.94(3H, s), 3.15(3H, s), 4.73(2H, s), 6.72(2H, d, J=9 Hz), 7.06(2H, d, J=9 Hz), 7.25(4H, s).

MS(m/z): 371(M$^+$), 265, 186, 107.

Preparation Example 10

A mixture composed of 80 mg of 4-[N-(4-hydroxybenzyl)-N-methylsulfonylamino]phenyl methanesulfonate and 0.5 ml of a 28% methanolic solution of sodium methoxide was stirred in 2 ml of methanol and 1 ml of tetrahydrofuran at 50° C. for 1hour. After hydrochloric acid was added to the reaction mixture, the product was extracted with ethyl acetate. The organic layer was washed with water and dried over anhydrous sodium sulfate. After the solvent was distilled off the resulting crude product was purified by TLC (using a 19:1 mixture of chloroform and methanol as the developing solvent) to obtain 38 mg of N-(4-hydroxybenzyl)-N-(4-hydroxyphenyl)methanesulfonamide.

$^1$H-NMR(CDCl$_3$, δ): 2.91(3H, s), 4.66(2H, s), 6.6–7.2 (8H, m).

MS(m/z): 293(M$^+$), 212, 187, 108.

Preparation Example 11

100 mg of 4-[N-(4-benzyloxybenzyl)amino]phenol was dissolved in 4 ml of pyridine, and 2 ml of acetic anhydride was added thereto, followed by stirring at room temperature for 2 hours. After water was added to the reaction mixture, the product was extracted with ethyl acetate. The organic layer was washed with 5% hydrochloric acid and a saturated aqueous solution of sodium hydrogen carbonate, and dried over anhydrous sodium sulfate. After the solvent was distilled off, the resulting crude product was purified by TLC (using chloroform as the developing solvent) to obtain 114 mg of 4-[N-acetyl-N-(4-benzyloxy-benzyl)amino]phenyl acetate.

$^1$H-NMR(CDCl$_3$, δ): 1.87(3H, s), 2.29(3H, s), 4.79(2H, s), 5.03(2H, s), 6.7–7.5(13H, m).

MS(m/z): 389(M$^+$), 197, 91.

Preparation Example 12

The procedure of Preparation Example 9 was repeated, except that 400 mg of 4-[N-acetyl-N-(4-benzyloxybenzyl) amino]phenyl acetate was used in place of 4-[N-(4-benzyloxybenzyl)-N-methylsulfonylamino]phenyl methanesulfonate, and 6 ml of ethanol was used in place of dioxane. Thus, there was obtained 270 mg of 4-[N-acetyl-N-(4-hydroxybenzyl)amino]phenyl acetate.

$^1$H-NMR(CDCl$_3$, δ): 1.88(3H, s), 2.29(3H, s), 4.78(2H, s), 6.6–7.3 (8H, m).

MS(m/z): 299(M$^+$), 193, 151, 109, 107.

Preparation Example 13

The procedure of Preparation Example 10 was repeated, except that 45 mg of 4-[N-acetyl-N-(4-hydroxybenzyl) amino]phenyl acetate was used in place of 4-[N-(4-hydroxybenzyl)-N-methylsulfonyl-amino]phenyl methanesulfonate. Thus, there was obtained 20 mg of N-(4-hydroxybenzyl)-N-(4-hydroxyphenyl)acetamide.

$^1$H-NMR(CDCl$_3$, δ): 1.84(3H, s), 4.72(2H, s), 6.70(2H, d, J=9 Hz), 6.74(4H, s), 6.98(2H, d, J=9 Hz).

MS(m/z): 257(M$^+$), 151, 109.

Preparation Example 14

A mixture composed of 600 mg of 4-methoxy-N-(4-methoxy-phenyl)benzamide and 150 mg of 60% sodium hydride was stirred in 7.5 ml of dimethyl sulfoxide at 50° C. for 10 minutes. Then, 1.05 ml of ethyl iodide was added, and the reaction mixture was stirred for 30 minutes. After water was added to the reaction mixture, the product was extracted with ethyl acetate. The organic layer was washed with water and dried over anhydrous sodium sulfate. After the solvent was distilled off, the resulting crude product was purified by TLC (using a 80:1 mixture of chloroform and acetone as the developing solvent) to obtain 591 mg of N-ethyl-4-methoxy-N-(4-methoxyphenyl)benzamide.

$^1$H-NMR(CDCl$_3$, δ): 1.19(3H, t, J=7 Hz), 3.73(3H, s), 3.75(3H, s), 3.90(2H, q, J=7 Hz), 6.5–7.4(8H, m).

MS(m/z): 285(M$^+$), 135.

Preparation Example 15

The procedure of Preparation Example 2 was repeated, except that 585 mg of N-ethyl-4-methoxy-N-(4-methoxyphenyl)benzamide was used in place of 4'-methoxy-2-biphenylacetonitrile. The resulting crude product was purified by TLC (using a 9:1 mixture of chloroform and methanol as the developing solvent) to obtain 466 mg of N-ethyl-4-hydroxy-N-(4-hydroxyphenyl) benzamide.

$^1$H-NMR(CDCl$_3$, δ): 1.17(3H, t, J=7 Hz), 3.87(2H, q, J=7 Hz), 6.4–7.3(8H, m).

MS(m/z): 257(M$^+$), 137, 121.

Preparation Example 16

The procedure of Preparation Example 14 was repeated, except that 1.2 ml of methyl iodide was used in place of ethyl iodide. Thus, there was obtained 629 mg of 4-methoxy-N-(4-methoxyphenyl)-N-methylbenzamide.

$^1$H-NMR(CDCl$_3$, δ): 3.43(3H, s), 3.74(3H, s), 3.75(3H, s), 6.5–7.3 (8H, m).

MS(m/z): 271(M$^+$), 135.

Preparation Example 17

The procedure of Preparation Example 2 was repeated, except that 603 mg of 4-methoxy-N-(4-methoxyphenyl)-N-methylbenzamide was used in place of 4'-methoxy-2- biphenylacetonitrile. The resulting crude product was purified by TLC (using a 9:1 mixture of chloroform and methanol as the developing solvent) to obtain 489 mg of 4-hydroxy-N-(4-hydroxyphenyl)-N-methylbenzamide.

$^1$H-NMR(CDCl$_3$, δ): 3.40(3H, s), 6.4–7.3(8H, m).

MS(m/z): 243(M$^+$), 123, 121.

Preparation Example 18

The procedure of Preparation Example 14 was repeated, except that 4-methoxy-N-(3-methoxyphenyl)benzamide was used in place of 4-methoxy-N-(4-methoxyphenyl)benzamide, and 1.2 ml of methyl iodide was used in place of ethyl iodide. Thus, there was obtained 625 mg of 4-methoxy-N-(3-methoxyphenyl)-N-methylbenzamide.

$^1$H-NMR(CDC$_3$, δ): 3.46(3H, s), 3.69(3H, s), 3.74(3H, s), 6.5–7.4 (8H, m).

MS(m/z): 271(M$^+$), 135.

Preparation Example 19

The procedure of Preparation Example 2 was repeated, except that 618 mg of 4-methoxy-N-(3-methoxyphenyl)-N-methylbenzamide was used in place of 4'-methoxy-2-biphenylacetonitrile. The resulting crude product was purified by TLC (using a 9:1 mixture of chloroform and methanol as the developing solvent) to obtain 442 mg of 4-hydroxy-N-(3-hydroxyphenyl)-N-methylbenzamide.

$^1$H-NMR(CDCl$_3$, δ): 3.42(3H, s), 6.4–7.3(8H, m).

MS(m/z): 243 (M$^+$), 123, 121.

Preparation Example 20

1.08 g of phenylhydrazine was dissolved in 10 ml of pyridine, and 0.78 g of acetic anhydride was added thereto under cooling with ice, followed by stirring for 20 minutes. Then, 2.0 g of 4-methoxybenzoyl chloride was added thereto, followed by stirring at room temperature for 15 hours. After water was added to the reaction mixture, the product was extracted with ethyl acetate. The organic layer was washed with 5% hydrochloric acid and a 5% aqueous solution of sodium hydroxide, and dried over anhydrous sodium sulfate. After the solvent was distilled off, the resulting crude product was purified by silica gel column chromatography (using a 40:1 mixture of chloroform and methanol as the eluent) to obtain 1.0 g of N'-acetyl-4-methoxy-N-phenylbenzohydrazide.

$^1$H-NMR(CDCl$_3$, δ): 2.07(3H, s), 3.76(3H, s), 6.72(2H, d, J=9 Hz), 7.21 (5H, s), 7.43(2H, d, J=9 Hz), 8.09(1H, br s).

MS(m/z): 284(M$^+$), 135.

Preparation Example 21

The procedure of Preparation Example 2 was repeated, except that 500 mg of N'-acetyl-4-methoxy-N-phenylbenzohydrazide was used in place of 4'-methoxy-2-biphenylacetonitrile. The resulting crude product was purified by TLC (using a 15:1 mixture of chloroform and methanol as the developing solvent) to obtain 224 mg of N'-acetyl-4-hydroxy-N-phenylbenzohydrazide.

$^1$H-NMR(CDCl$_3$+CD$_3$OD, δ): 2.04(3H, 9), 6.66(2H, d, J=9 Hz), 7.21 (5H, s), 7.35(2H, d, J=9 Hz).

MS(m/z): 270(M$^+$), 121.

Preparation Example 22

A mixture composed of 167 mg of 4-(tert-butyldimethylsilyloxy)benzylalcohol and 1 ml of thionyl chloride was heated under reflux for 1 hour. After the thionyl chloride was distilled off from the reaction mixture under reduced pressure, its azeotropic distillation with toluene was carried out three times to remove any thionyl chloride. The resulting residue was dissolved in 4.3 ml of acetonitrile, and 108 mg of 4-[N-(1,2,4-triazol-4-yl)amino]benzonitrile and 172 mg of potassium carbonate were added thereto, followed by stirring at room temperature for 18 hours. After water was added to the reaction mixture and neutralized with dilute hydrochloric acid, the product was extracted with ethyl acetate. After the extract was washed with water and dried over anhydrous sodium sulfate, the solvent was distilled off under reduced pressure. The resulting crude product was purified by silica gel column chromatography (using a 9:1 mixture of chloroform and methanol as the eluent) to obtain 102 mg of 4-[N-(4-hydroxybenzyl)-N-(1,2,4-triazol-4-yl)amino]benzonitrile.

$^1$H-NMR(DMSO-d$_6$, δ): 4.89(2H, s), 6.6–6.8(4H, m), 7.04(2H, d, J=8.6 Hz), 7.72(2H, d, J=9.0 Hz), 8.65(2H, s), 9.40(1H, s).

MS(m/z): 291(M$^+$), 185.

Preparation Example 23

A mixture composed of 10.43 g of 4-[N-(1,2,4-triazol-4-yl)amino]benzonitrile, 7.9 ml of triethylamine, and 56 ml of methylene chloride was stirred under cooling with ice, and a mixture composed of 23.7 g of 4-(trimethylsilyloxy)benzoyl chloride and 28 ml of methylene chloride was added dropwise thereto, followed by stirring at room temperature for 1 hour. Dilute hydrochloric acid was added to the reaction mixture, followed by stirring at room temperature overnight. After the reaction mixture was neutralized with a saturated aqueous solution of sodium hydrogen carbonate, the product was extracted with tetrahydrofuran-diethyl ether (1:1). After the extract was washed with water and dried over anhydrous sodium sulfate, the solvent was distilled off under reduced pressure. The resulting crude product was purified by silica gel column chromatography (using a 4:1 mixture of chloroform and acetone as the eluent) to obtain 6.2 g of N-(4-cyanophenyl)-4-hydroxy-N-(1,2,4-triazol-4-yl)benzamide.

$^1$H-NMR(DMSO-d$_6$, δ): 6.71(2H, d, J=8.8 Hz), 7.38(2H, d, J=8.8 Hz), 7.46(2H, d, J=8.8 Hz), 7.86(2H, d, J=8.8 Hz), 9.05(2H, s), 10.21 (1H, br s).

MS(m/z): 305(M$^+$), 185.

Preparation Example 24

The procedure of Example 1 was repeated, except that 244 mg of 4-hydroxybenzaldehyde was used in place of 2'-nitrobiphenyl-4-ol. The resulting crude product was purified by silica gel column chromatography (using a 19:1 mixture of chloroform and acetone as the eluent) to obtain 203 mg of 4-formylphenyl sulfamate.

$^1$H-NMR(CDC$_3$, δ): 7.50(2H, d, J=8.6 Hz), 7.94(2H, d, J=9.0 Hz), 10.00(1H, s).

MS(m/z): 201(M$^+$), 121.

Preparation Example 25

A mixture composed of 286 mg of 4-(tert-butyldimethylsilyloxy)benzyl alcohol and 1.75 ml of thionyl chloride was heated under reflux for 1 hour. After the thionyl chloride was distilled off from the reaction mixture under reduced pressure, its azeotropic distillation with toluene was carried out three times to remove any thionyl chloride. Thus, there was obtained 4-(tert-butyldimethylsilyloxy)benzyl chloride.

224 mg of 4-[N(4-methoxyphenyl)amino]benzonitrile was dissolved in 1.2 ml of N,N-dimethylformamide, and 48 mg of sodium borohydride was added thereto under cooling with ice, followed by stirring at room temperature for 30 minutes. The previously prepared 4-(t-butyldimethylsilyloxy)benzyl chloride was dissolved in 1.2 ml of N,N- dimethylformamide and added to the reaction mixture under cooling with ice, followed by stirring at room temperature for 2 days. After water was added to the reaction mixture, the product was extracted with ethyl acetate. After the extract was washed with water and dried over anhydrous sodium sulfate, the solvent was distilled off under reduced pressure. The resulting residue was dissolved in 1.2 ml of tetrahydrofuran, and 1.2 ml of a 1 M tetrahydrofuran solution of tetrabutylammonium fluoride was added thereto, followed by stirring at room temperature for 15 minutes. After a saturated aqueous solution of sodium hydrogen carbonate was added to the reaction mixture, the product was extracted with ethyl acetate. After the extract was washed with water and dried over anhydrous sodium sulfate, the solvent was distilled off under reduced pressure. The resulting crude product was purified by silica gel column chromatography (using ethyl acetate as the eluent) to obtain 229 mg of 4-[N-(4-hydroxybenzyl)-N-(4-methoxyphenyl)amino]benzonitrile.

$^1$H-NMR(CDCl$_3$, δ): 3.82(3H, s), 4.7–5.0(3H, m), 6.4–7.4(12H, m).

MS(m/z): 330(M$^+$), 224.

Preparation Example 26

The procedure of Preparation Example 25 was repeated, except that 194 mg of 4-(N-phenylamino)benzonitrile was used in place of 4-[N-(4-methoxyphenyl)amino]benzonitrile. Thus, there was obtained 172 mg of 4-[N-(4-hydroxybenzyl)-N-phenylamino]benzonitrile.

$^1$H-NMR(CDCl$_3$, δ): 4.9(2H, br s), 5.1–6.4(1H, br), 6.7–7.9(13H, m).

MS(m/z): 300(M$^+$), 194.

Preparation Example 27

The procedure of Preparation Example 22 was repeated, except that 219 mg of 4,4'-iminobisbenzonitrile was used in place of 4-[N-(1,2,4-triazol-4-yl)amino]benzonitrile. The resulting crude product was purified by silica gel column chromatography (using a 7:1 mixture of hexane and ethyl acetate as the eluent) to obtain 95 mg of N-[4-(tert-butyldimethylsilyloxy)benzyl]-4,4'-iminobisbenzonitrile.

Then, 92 mg of N-[4-(tert-butyldimethylsilyloxy)benzyl]-4,4'-iminobisbenzonitrile was dissolved in 0.21 ml of tetrahydrofuran, and 0.21 ml of a 1 M tetrahydrofuran solution of tetrabutylammonium fluoride was added thereto, followed by stirring at room temperature for 30 minutes. After a saturated aqueous solution of sodium hydrogen carbonate was added to the reaction mixture, the product was extracted with ethyl acetate. After the extract was washed with water and dried over anhydrous sodium sulfate, the solvent was distilled off under reduced pressure. The resulting crude product was purified by TLC (using a 39:1 mixture of chloroform and acetone as the developing solvent) to obtain 54 mg of N-(4-hydroxybenzyl)-4,4'-iminobisbenzonitrile.

$^1$H-NMR(CDCl$_3$, δ): 4.8–5.1(3H, m), 6.7–7.6(12H, m).

MS(m/z): 325(M$^+$), 219.

Preparation Example 28

900 mg of metallic potassium was mixed with 40 ml of tert-butanol under an atmosphere of nitrogen, and this mixture was heated under reflux to form a homogeneous solution. After the solvent was distilled off from the reaction mixture under an atmosphere of nitrogen, its azeotropic distillation with toluene was carried out twice. The resulting residue was dried under reduced pressure to prepare potassium tert-butoxide.

10 ml of dimethyl sulfoxide was added to the above potassium tert-butoxide, followed by cooling in an ice-water bath. While this mixture was kept at 20° C. or below, 1.882 g of 4-aminopyridine was added thereto, followed by stirring at room temperature for 1 hour. 1.21 g of 4-fluorobenzonitrile was dissolved in 3 ml of dimethyl sulfoxide, and this solution was added dropwise to the above reaction mixture kept at an internal temperature of 30° C. or below, followed by stirring at room temperature for 30 minutes. After water was added to the reaction mixture, the resulting mixture was acidified with dilute hydrochloric acid and then neutralized with a saturated aqueous solution of sodium hydrogen carbonate. The product was extracted with tetrahydrofuran-diethyl ether (1:1), and the organic layer was washed with water and dried over anhydrous sodium sulfate. After the solvent was distilled off, the resulting crude product was purified by silica gel column chromatography (using a 9:1 mixture of chloroform and methanol as the eluent) to obtain 1.85 g of 4-[N-(4-pyridyl)amino]benzonitrile.

$^1$H-NMR(DMSO-d$_6$, δ): 7.0–7.2(2H, m), 7.30(2H, d, J=8.1 Hz), 7.71(2H, d, J=8.8 Hz), 7.9–8.1(2H, m).

MS(m/z): 195(M$^+$).

Preparation Example 29

The procedure of Preparation Example 22 was repeated, except that 114 mg of 4-[N-(4-pyridyl)amino]benzonitrile was used in place of 4-[-(1,2,4-triazol-4-yl)amino]benzonitrile. The resulting crude product was purified by TLC (using a 9:1 mixture of chloroform and methanol as the developing solvent) to obtain 48 mg of 4-[N-[4-(tert-butyldimethylsilyloxy)benzyl]-N-(4-pyridyl)amino]benzonitrile.

Then, 31 mg of 4-[N-[4-(tert-butyldimethylsilyloxy)benzyl]-N-(4-pyridyl)amino]benzonitrile was dissolved in 0.33 ml of tetrahydrofuran, and 0.15 ml of a 1 M tetrahydrofuran solution of tetrabutyl-ammonium fluoride was added thereto, followed by stirring at room temperature for 45 minutes. After water was added to the reaction mixture, the product was extracted with tetrahydrofuran-diethyl ether (1:1). After the extract was washed with water and dried over anhydrous sodium sulfate, the solvent was distilled off under reduced pressure. The resulting crude product was purified by TLC (using a 9:1 mixture of chloroform and methanol as the developing solvent) to obtain 14 mg of 4-[N-(4-hydroxybenzyl)-N-(4-pyridyl)amino]benzonitrile.

$^1$H-NMR(CDCl$_3$, δ): 4.96(2H, s), 6.7–6.9(4H, m), 7.03 (2H, d, J=8.8 Hz), 7.33(2H, d, J=8.3 Hz), 7.63(2H, d, J=9.0 Hz), 8.22(2H, br d, J=6.4 Hz).

MS(m/z): 301(M$^+$), 195.

Preparation Example 30

The procedure of Example 40 was repeated, except that 3.58 g of 4-aminobenzonitrile was used in place of aniline, and 4.62 g of 4-hydroxybenzaldehyde was used in place of 4-formylphenyl sulfamate. The resulting crude product was purified by silica gel column chromatography (using a 39:1 mixture of chloroform and acetone as the eluent) to obtain 3.37 g of 4-[N-(4-hydroxybenzyl)amino]-benzonitrile.

¹H-NMR(CDCl₃, δ): 4.25(2H, s), 6.59(2H, d, J=9.0 Hz), 6.82(2H, d, J=8.6 Hz), 7.16(2H, d, J=8.6 Hz), 7.40(2H, d, J=8.8 Hz).

MS(m/z): 224(M⁺), 118.

Preparation Example 31

224 mg of 4-[N-(4-hydroxybenzyl)amino]benzonitrile, 0.28 ml of triethylamine, and 7 ml of tetrahydrofuran were mixed, and 178 mg of nicotinoyl chloride hydrochloride was slowly added thereto, followed by stirring at room temperature overnight. After water was added to the reaction mixture, the product was extracted with tetrahydrofuran-diethyl ether (1:1). After the extract was washed with water and dried over anhydrous sodium sulfate, the solvent was distilled off under reduced pressure. The resulting crude product was purified by TLC (using a 9:1 mixture of chloroform and acetone as the developing solvent) to obtain 292 mg of N-(4-cyanophenyl)-N-(4-hydroxybenzyl)-nicotinamide.

¹H-NMR(CDCl₃, δ): 4.2–4.7(3H, m), 6.61(2H, d, J=8.8 Hz), 7.1–7.7 (7H, m), 8.44(1H, dt, J=2.0, 8.0 Hz), 8.86(1H, dd, J=1.8, 4.8 Hz), 9.39(1H, d, J=1.5 Hz).

MS(m/z): 329(M⁺), 223.

Preparation Example 32

Reaction was carried out in the same manner as in Preparation Example 31, except that 0.116 ml of benzoyl chloride was used in place of nicotinoyl chloride hydrochloride. The resulting crude product was purified by TLC (using chloroform as the developing solvent) to obtain 337 mg of N-(4-cyanophenyl)-N-(4-hydroxybenzyl)benzamide.

¹H-NMR(CDCl₃, δ): 4.39(2H, s), 4.5(1H, br), 6.61(2H, d, J9 Hz), 7.1–7.7(9H, m), 8.19(2H, dd, J=1.8, 7.9 Hz).

MS(m/z): 328(M⁺).

Preparation Example 33

Reaction was carried out in the same manner as in Preparation Example 31, except that 166 mg of 4-cyanobenzoyl chloride was used in place of nicotinoyl chloride hydrochloride. The resulting crude product was purified by TLC (using chloroform as the developing solvent) to obtain 344 mg of 4-cyano-N-(4-cyanophenyl)-N-(4-hydroxybenzyl)benzamide.

¹H-NMR(DMSO-d₆, δ):4.39(2H, d, J=5.9 Hz), 6.68(2H, d, J=8.8 Hz), 6.8–8.0(7H, m), 8.09(2H, d, J=8.1 Hz), 8.25 (2H, d, J=8.4 Hz).

MS(m/z): 353(M⁺), 247.

Preparation Example 34

825 mg of 4-cyanobenzoyl chloride was dissolved in 9 ml of dichloroethane, and mixed with 0.69 ml of 4-methoxybenzylamine and 1.57 ml of triethylamine, followed by stirring for 2.5 hours. Thereafter, the reaction was stopped by the addition of 1 ml of distilled water. After the product was extracted with chloroform, the extract was successively washed with 2 N hydrochloric acid, a saturated aqueous solution of sodium hydrogen carbonate, and a saturated aqueous solution of sodium chloride, and dried over anhydrous sodium sulfate. After the solvent was distilled off, the resulting crude product was purified by silica gel column chromatography (using a 20:1 mixture of chloroform and acetone as the eluent) to obtain 1.29 g of 4-cyano-N-(4-methoxy-benzyl)benzamide.

¹H-NMR(CDCl₃, δ): 3.80(3H, s), 4.55(2H, d, J=6.0 Hz), 6.2–6.5(1H, br), 6.88(2H, d, J=8.6 Hz), 7.27(2H, d, J=8.8 Hz), 7.60–8.05(4H, m).

MS(m/z): 266(M⁺), 235.

Preparation Example 35

79 mg of 4-cyano-N-(4-methoxybenzyl)benzamide was dissolved in 2.5 ml of tetrahydrofuran, and 24 mg of 60% sodium hydride was added thereto, followed by heating under reflux for 5 minutes in an atmosphere of nitrogen. After cooling, 0.1 ml of methyl iodide was added thereto, followed by stirring for 15 minutes. Thereafter, the reaction was stopped by the addition of 1 ml of distilled water. After the product was extracted with ethyl acetate, the extract was successively washed with 2 N hydrochloric acid, a saturated aqueous solution of sodium hydrogen carbonate, and a saturated aqueous solution of sodium chloride, and dried over anhydrous sodium sulfate. After the solvent was distilled off, the resulting crude product was purified by TLC (using a 1:1 mixture of ethyl acetate and hexane as the developing solvent) to obtain 72 mg of 4-cyano-N-(4-methoxybenzyl)-N-methylbenzamide.

¹H-NMR(CDCl₃, δ): 2.68–3.17(3H, m), 3.81(3H, s), 4.30–4.80(2H, m), 6.88(2H, d, J=8.6 Hz), 7.0–7.4(2H, m), 7.51(2H, d, J=6.4 Hz), 7.70(2H, d, J=8.4 Hz).

MS(m/z): 280(M⁺), 265.

Preparation Example 36

The procedure of Preparation Example 2 was repeated, except that 71 mg of 4-cyano-N-(4-methoxybenzyl)-N-methylbenzamide was used in place of 4'-methoxy-2-biphenylacetonitrile, and toluene was used in place of methylene chloride. The resulting crude product was purified by TLC (using a 4:1 mixture of chloroform and acetone as the developing solvent) to obtain 53 mg of 4-cyano-N-(4-hydroxybenzyl)-N-methylbenzamide.

¹H-NMR(CDCl₃, δ): 2.68–3.20(3H, m), 4.20–4.77(2H, m), 6.80(2H, d, J=8.6 Hz), 6.9–7.4(2H, m), 7.51(2H, d, J=8.6 Hz), 7.70(2H, d, J=8.6 Hz).

MS(m/z): 266(M⁺), 251.

Preparation Example 37

The procedure of Preparation Example 34 was repeated, except that 101 mg of 4-[N-(1,2,4-triazol-4-yl)aminomethyl]phenol was used in place of 4-methoxybenzylamine, and 105 mg of 3-cyanobenzoyl chloride was used in place of 4-cyanobenzoyl chloride. The resulting crude product was purified by TLC (using a 10:1 mixture of chloroform and methanol as the developing solvent) to obtain 26 mg of 3-cyano-N-(4-hydroxybenzyl)-N-(1,2,4-triazol-4-yl)benzamide.

¹H-NMR(CD₃OD, δ): 4.97(2H, s), 6.47 and 7.01(2H, J_{AB}=6.8 Hz), 8.41(2H, s).

MS(m/z): 319(M⁺), 251.

Preparation Example 38

190 mg of 4-[N-(3-pyridyl)amino]benzonitrile was dissolved in 5 ml of N,N-dimethylformamide, and 44 mg of 60% sodium hydride was added thereto under cooling with ice, followed by stirring at 40–50° C. for 30 minutes. Then, 273 mg of 4-benzyloxybenzyl chloride was added to the reaction mixture under cooling with ice, followed by stirring at room temperature for 2 hours. After the reaction mixture was poured into water, the product was extracted with chloroform. After the extract was washed with water and dried over anhydrous magnesium sulfate, the solvent was distilled off under reduced pressure. The resulting crude product was purified by TLC (using a 1:1 mixture of ethyl acetate and hexane as the developing solvent) to obtain 234 mg of 4-[N-(4-benzyloxy-benzyl)-N-(3-pyridyl)amino]benzonitrile.

$^1$H-NMR(CDCl$_3$, δ): 4.93(2H, s), 5.03(2H, s), 6.67–7.63 (15H, m), 8.44(1H, dd, J=1.2, 3.0 Hz), 8.54(1H, d, J=1.5 Hz).

MS(m/z): 391(M$^+$).

Preparation Example 39

The procedure of Preparation Example 9 was repeated, except that 222 mg of 4-[N-(4-benzyloxybenzyl)-N-(3-pyridyl)amino]benzonitrile was used in place of 4-[N-(4-benzyloxybenzyl)-N-methylsulfonylamino]-phenyl methanesulfonate, and 3 ml of ethyl acetate was used in place of dioxane. The resulting mixture was stirred for 3 days under an atmospheric pressure of hydrogen. The reaction mixture was filtered to remove any insoluble matter, and the solvent was distilled off from the filtrate. The resulting crude product was purified by TLC (using a 1:1 mixture of ethyl acetate and hexane as the developing solvent) to obtain 95 mg of 4-[N-(4-hydroxybenzyl)-N-(3-pyridyl)amino]benzonitrile.

$^1$H-NMR(CDCl$_3$, δ): 4.92(2H, s), 6.58–7.70(10H, m), 8.39(1H, dd, J=1.2, 3.2 Hz), 8.48(1H, d, J=1.5 Hz).

MS(m/z): 301(M$^+$).

Preparation Example 40

The procedure of Preparation Example 7 was repeated, except that 2.95 g of 4-aminobenzonitrile was used in place of 4-aminophenol. The resulting crude product was purified by silica gel column chromatography (using a 4:1 mixture of hexane and ethyl acetate as the eluent) to obtain 5.194 g of 4-[-(4-benzyloxybenzyl)amino]-benzonitrile.

$^1$H-NMR(CDCl$_3$, δ): 4.40(2H, d, J=3.0 Hz), 4.4(1H, br), 5.06(2H, s), 6.56(2H, d, J=5.8 Hz), 6.78–7.52(11H, m).

MS(m/z): 314(M$^+$).

Preparation Example 41

The procedure of Preparation Example 38 was repeated, except that 314 mg of 4-[N-(4-benzyloxybenzyl)amino]benzonitrile was used in place of 4-[N-(3-pyridyl)amino]benzonitrile, and 142 mg of methyl iodide was used in place of 4-benzyloxybenzyl chloride. The resulting crude product was purified by TLC (using a 2:1 mixture of hexane and ethyl acetate as the developing solvent) to obtain 173 mg of 4-[N-(4-benzyloxybenzyl)-N-methylamino]benzonitrile.

$^1$H.NMR(CDCl$_3$, δ): 3.08(3H, s), 4.56(2H, d, J=5.8 Hz), 5.05(2H, s), 6.42–7.55(13H, m).

MS(m/z): 328(M$^+$).

Preparation Example 42

The procedure of Preparation Example 9 was repeated, except that 164 mg of 4-[N(4-benzyloxybenzyl)-N-methylamino]benzontrile was used in place of 4-[N-(4-benzyloxybenzyl)-N-methylsulfonylamino]-phenyl methanesulfonate, and 3 ml of ethyl acetate was used in place of dioxane. The resulting mixture was stirred for 4 hours under an atmospheric pressure of hydrogen. The reaction mixture was filtered to remove any insoluble matter, and the solvent was distilled off from the filtrate. The resulting crude product was purified by TLC (using a 1:1 mixture of ethyl acetate and hexane as the developing solvent) to obtain 44 mg of 4-[N-(4-hydroxybenzyl)-N-methylamino]benzonitrile.

$^1$H-NMR(CDCl$_3$, δ): 3.09(3H, s), 4.52(2H, s), 6.43–7.57 (8H, m).

MS(m/z): 238(M$^+$).

Preparation Example 43

The procedure of Preparation Example 38 was repeated, except that 314 mg of 4-[N-(4-benzyloxybenzyl)amino]benzonitrile was used in place of 4-[N-(3-pyridyl)amino]benzonitrile, and 156 mg of ethyl iodide was used in place of 4-benzyloxybenzyl chloride. The resulting crude product was purified by TLC (using a 2:1 mixture of hexane and ethyl acetate as the developing solvent) to obtain 114 mg of 4-[N-(4-benzyloxybenzyl)-N-ethylamino]benzonitrile.

$^1$H-NMR(CDCl$_3$, δ): 1.22(3H, t, J=4.7 Hz), 3.50(2H, q, J=4.7 Hz), 4.55(2H, d, J=5.8 Hz), 5.05(2H, s), 6.64(2H, d, J=6.0 Hz), 6.93(2H, d, J=5.3 Hz), 7.07(2H, d, J=6.0 Hz), 7.17–7.56(7H, m).

MS(m/z): 342(0).

Preparation Example 44

The procedure of Preparation Example 9 was repeated, except that 111 mg of 4-[N-(4-benzyloxybenzyl)-N-ethylamino]benzonitrile was used in place of 4-[N-(4-benzyloxybenzyl)-N-methylsulfonylamino]phenyl methanesulfonate, and 3 ml of ethyl acetate was used in place of dioxane. The resulting mixture was stirred for 4 hours under an atmospheric pressure of hydrogen. The reaction mixture was filtered to remove any insoluble matter, and the solvent was distilled off from the filtrate. The resulting crude product was purified by TLC (using a 1:1 mixture of ethyl acetate and hexane as the developing solvent) to obtain 29 mg of 4-[N-ethyl-N-(4-hydroxybenzyl)amino]benzonitrile.

$^1$H-NMR(CDC$_3$, δ): 1.22(3H, t, J=4.7 Hz), 3.50(2H, q, J=4.7 Hz), 4.49(2H,s), 6.45–7.55(8H, m).

MS(m/z): 252(M$^+$).

Preparation Example 45

The procedure of Preparation Example 7 was repeated, except that 2.058 g of 4-(tert-butyldimethylsilyloxy)benzyl chloride was used in place of 4-benzyloxybenzyl chloride, and 0.946 g of 4-aminobenzonitrile was used in place of 4-aminophenol. The resulting crude product was purified by silica gel column chromatography (using a 3:1 mixture of hexane and ethyl acetate as the eluent) to obtain 0.682 g of 4-[N-(4-tert-butyldimethylsilyloxybenzyl)amino]benzonitrile.

$^1$H-NMR(CDCl$_3$, δ):0.17(6H, s), 0.96(9H, s), 4.23(2H, d, J=5.2 Hz), 4.6(1H, br), 6.63(2H, d, J=8.4 Hz), 6.79(2H, d, J=8.21 Hz), 7.17(2H, d, J=8.2 Hz), 7.33(2H, d, J=8.4 Hz).

Preparation Example 46

The procedure of Preparation Example 8 was repeated, except that 195 mg of 4-[N-(4-tert-butyldimethylsilyloxybenzyl)amino]benzonitrile was used in place of 4-[N-(4-benzyloxybenzyl)amino]phenol, and 84 mg of 2-thiophenecarbonyl chloride was used in place of methanesulfonyl chloride. The resulting mixture was stirred at room temperature for 19 hours. After the reaction mixture was poured into dilute hydrochloric acid, the product was extracted with ethyl acetate. After the extract was successively washed with a saturated aqueous solution of sodium hydrogen carbonate and a saturated aqueous solution of sodium chloride, and dried over anhydrous magnesium sulfate, the solvent was distilled off under reduced pressure. The resulting crude product was purified by TLC (using a 3:1 mixture of hexane and ethyl acetate as the developing solvent) to obtain 196 mg of N-(4-tert-butyldimethylsilyloxybenzyl)-N-(4-cyanophenyl)-2-thiophenecarboxamide.

$^1$H-NMR(CDCl$_3$, δ):0.17(6H, s), 0.96(9H, s), 5.00(2H, s), 6.60–7.67(11H, m).

MS(m/z): 448(M$^+$).

Preparation Example 47

180 mg of N-(4-tert-butyldimethylsilyloxybenzyl)-N-(4-cyanophenyl)-2-thiophenecarboxamide was dissolved in 3.5 ml of tetrahydrofuran, and 386 mg of tetrabutylammonium fluoride was added thereto under cooling with ice, followed by stirring at room temperature for 4 hours. After the reaction mixture was poured into a saturated aqueous solution of sodium chloride, the product was extracted with diethyl ether. After the extract was dried over anhydrous magnesium sulfate, the solvent was distilled off under reduced pressure. The resulting crude product was purified by TLC (using a 19:1 mixture of chloroform and methanol as the developing solvent) to obtain 47 mg of N-(4-cyanophenyl)-N-(4-hydroxybenzyl)-2-thiophenecarboxamide.

$^1$H-NMR(CD$_3$OD, δ): 5.02(2H, s), 6.56–7.76(11H, m).

MS(m/z): 334(M$^+$).

Preparation Example 48

The procedure of Preparation Example 8 was repeated, except that 203 mg of 4-[N-(4-tert-butyldimethylsilyloxybenzyl)amino]benzonitrile was used in place of 4-[N-(4-benzyloxybenzyl)amino]phenol and 110 mg of 3-thiophenecarbonyl chloride was used in place of methanesulfonyl chloride. The resulting mixture was stirred at room temperature for 19 hours. After the reaction mixture was poured into dilute hydrochloric acid, the product was extracted with ethyl acetate. After the extract was successively washed with a saturated aqueous solution of sodium hydrogen carbonate and a saturated aqueous solution of sodium chloride, and dried over anhydrous magnesium sulfate, the solvent was distilled off under reduced pressure. The resulting crude product was purified by TLC (using a 3:1 mixture of hexane and ethyl acetate as the developing solvent) to obtain 191 mg of N-(4-tert-butyl-dimethylsilyloxybenzyl)-N-(4-cyanophenyl)-3thiophenecarboxamide.

$^1$H-NMR(CDCl$_3$, δ): 0.17(6H, s), 0.96(9H, s), 5.03(2H, s), 6.61–7.60(11H, m).

MS(m/z): 448(M$^+$).

Preparation Example 49

The procedure of Preparation Example 47 was repeated, except that 180 mg of N-(4-tert-butyldimethylsilyloxybenzyl)-N-(4-cyanophenyl)-3-thiophenecarboxamide was used in place of N-(4-tert-butyldimethylsilyloxybenzyl)-N-(4-cyanophenyl)-2-thiophenecarboxamide. Thus, there was obtained 60 mg of N-(4-cyanophenyl)-N-(4-hydroxy-benzyl)-3-thiophenecarboxamide.

$^1$H-NMR(CD$_6$OD, δ): 5.04(2H, s), 6.55–7.70(11H, m).

MS(m/z): 334(M$^+$).

Preparation Example 50

The procedure of Preparation Example 38 was repeated, except that 504 mg of N-(4-cyanophenyl)-4-methoxybenzamide was used in place of 4-[N-(3-pyridyl)amino]benzonitrile, and 707 mg of methyl iodide was used in place of 4-benzyloxybenzyl chloride. Thus, there was obtained 620 mg of a crude product of N-(4-cyanophenyl)-4-methoxy-N-methylbenzamide.

$^1$H-NMR(CDCl$_3$, δ): 3.45(3H, s), 3.72(3H, s), 6.70(2H, d, J=8.4 Hz), 7.15(2H, d, J=8.4 Hz), 7.23(2H, d, J=8.4 Hz), 7.55(2H, d, J=8.4 Hz).

Preparation Example 51

The procedure of Preparation Example 2 was repeated, except that 556 mg of N-(4-cyanophenyl)-4-methoxy-N-methylbenzamide was used in place of 4'-methoxy-2-biphenylacetonitrile. Thus, there was obtained 463 mg of a crude product of N-(4-cyanophenyl)-4-hydroxy-N-methylbenzamide.

$^1$H-NMR(DMSO-d$_6$, δ): 3.27(3H, s), 6.42–7.40 (8H, m).

MS(m/z): 252(M$^+$).

Preparation Example 52

451 mg of 3-methoxy-N-(2-methoxyphenyl)benzamide and 1.58 g of pyridine hydrochloride were mixed, and stirred on an oil bath at 190° C. for 2 hours. After cooling, dilute hydrochloric acid was added to the reaction mixture, and the product was extracted with ethyl acetate. The extract was washed with a saturated aqueous solution of sodium hydrogen carbonate and dried over anhydrous sodium sulfate. After the solvent was distilled oft the resulting crude product was recrystallized from methanol to obtain 109 mg of 3-hydroxy-N-(2-hydroxyphenyl)benzamide.

$^1$H-NMR(DMSO-d$_6$, δ): 6.9–7.1 (1H, m), 7.2–7.9(9H, m), 9.90(1H, s).

MS(m/z): 211(M$^+$—H$_2$O).

Preparation Example 53

The procedure of Preparation Example 52 was repeated, except that 536 mg of 3-methoxy-N-(4-methoxyphenyl)benzamide was used in place of 3-methoxy-N-(2-methoxyphenyl)benzamide. The resulting crude product was crystallized from diethyl ether to obtain 127 mg of 3-hydroxy-N-(4-hydroxyphenyl)benzamide.

$^1$H-NMR(DMSO-d$_6$, δ): 6.73(2H, d, J=7 Hz), 6.8–7.4 (4H, m), 7.50(2H, d, J=8.8 Hz), 9.4(2H, br), 9.87(1H, br s).

MS(m/z): 229(M$^+$), 121.

Preparation Example 54

The procedure of Preparation Example 25 was repeated, except that 392 mg of 4-[N-(2-pyrazinyl)amino]benzonitrile was used in place of 4-[N-(4-methoxyphenyl)amino]benzonitrile. Thus, there was obtained 445 mg of 4-[N-(4-hydroxybenzyl)-N-(2-pyrazinyl)amino]benzonitrile.

$^1$H-NMR(CD$_3$OD, δ): 5.19(2H, s), 6.68(2H, d, J=5.5 Hz), 7.06(2H, d, J=5.5 Hz), 7.40(2H, d, J=5.8 Hz), 7.67(2H, d, J=5.8 Hz) 7.80–8.27 (3H, m).

MS(m/z): 302(M$^+$).

Preparation Example 55

The procedure of Example 40 was repeated, except that 1.43 g of 4-aminobenzonitrile was used in place of aniline, and 1.57 g of 2-thiophenecarbaldehyde was used in place of 4-formyl-phenyl sulfamate. The resulting crude product was purified by silica gel column chromatography (using a 2:1 mixture of hexane and ethyl acetate as the eluent) to obtain 0.98 g of 4-[N-(2-thenyl)amino]-benzonitrile.

¹H-NMR(CDCl₃, δ): 4.56(2H, s), 6.46–6.76(2H, m), 6.87–7.83(5H, m).

MS(m/z): 214(M⁺).

Preparation Example 56

The procedure of Preparation Example 25 was repeated, except that 428 mg of 4-[N-(2-thenyl)amino]benzonitrile was used in place of 4-[N-(4-methoxyphenyl)amino] benzonitrile. Thus, there was obtained 349 mg of 4-[N-(4-hydroxybenzyl)-N-(2-thenyl)amino]benzonitrile.

¹H-NMR(CD₃OD, δ): 4.60(2H, s), 4.83(2H, s), 6.55–7.55 (11H, m).

MS(m/z): 320(M⁺).

Preparation Example 57

The procedure of Example 40 was repeated, except that 1.43 g of 4-aminobenzonitrile was used in place of aniline, and 1.57 g of 3-thiophenecarbaldehyde was used in place of 4-formyl-phenyl sulfamate. The resulting crude product was purified by silica gel column chromatography (using a 2:1 mixture of hexane and ethyl acetate as the eluent) to obtain 1.00 g of 4-[N-(3-thenyl)amino]-benzonitrile.

¹H-NMR(CDCl₃, δ): 4.40(2H, 8), 6.44–6.73(2H, m), 6.90–7.56(5H, m).

MS(m/z): 214(M⁺).

Preparation Example 58

The procedure of Preparation Example 25 was repeated, except that 428 mg of 4-[N-(3-thenyl)amino]benzonitrile was used in place of 4-[N-(4-methoxyphenyl)amino] benzonitrile. Thus, there was obtained 391 mg of 4-[N-(4-hydroxybenzyl)-N-(3-thenyl)amino]benzonitrile.

¹H-NMR(CD₃OD, δ): 4.62(2H, s), 4.67(2H, s), 6.60–7.53 (11H, m).

MS(m/z): 320(M⁺).

Preparation Example 59

A mixture composed of 500 mg of N-(4-bromophenyl) methane-sulfonamide, 334 mg of 4-methoxyphenyl boronic acid, 55.5 mg of tetrakis-triphenylphosphinepalladium, 2 ml of a 2 M aqueous solution of sodium carbonate, 4 ml of toluene, and 1 ml of ethanol was heated under. reflux for 5 hours in an atmosphere of nitrogen. After the reaction mixture was poured into a saturated aqueous solution of sodium chloride, the product was extracted with ethyl acetate. The organic layer was washed with water and dried over anhydrous magnesium sulfate. After the solvent was distilled off, the resulting crude product was purified by silica gel column chromatography (using a 7:1 mixture of chloroform and tetrahydrofuran as the eluent) to obtain 94 mg of N-(4'-methoxybiphenyl-4-yl)methanesulfonamide.

¹H-NMR(DMSO-d₆, δ): 2.98(3H, s), 3.79(3H, s), 7.00 (2H, d, J=8.7 Hz), 7.26(2H, d, J=8.7 Hz), 7.55(2H, d, J=8.7 Hz), 7.57(2H, d, J=8.7 Hz), 9.72(1H, s).

MS(m/z): 277(M⁺), 198.

Preparation Example 60

The procedure of Preparation Example 2 was repeated, except that 55 mg of N-(4'-methoxybiphenyl-4-yl) methanesulfonamide was used in place of 4'-methoxy-2-biphenylacetonitrile, and 1,2-dichloroethane was used in place of methylene chloride. The resulting crude product was purified by TLC (using a 6:1 mixture of chloroform and acetone as the developing solvent) to obtain 24 mg of N-(4'-hydroxybiphenyl-4-yl)-methanesulfonamide.

¹H-NMR(DMSO-d₆, δ): 2.98(3H, s), 6.82(2H, d, J=8.7 Hz), 7.24(2H, d, J=8.7 Hz), 7.43(2H, d, J=8.7 Hz), 7.53(2H, d, J=8.7 Hz), 9.45(1H, s), 9.69(1H, s).

MS(m/z): 263(M⁺), 184.

Preparation Example 61

The procedure of Preparation Example 59 was repeated, except that 500 mg of N-(2-bromophenyl) methanesulfonamide was used in place of N-(4-bromophenyl)methanesulfonamide. The resulting crude product was purified by TLC (using a 2:1 mixture of hexane and ethyl acetate as the developing solvent) to obtain 441 mg of N-(4'-methoxybiphenyl-2-yl)methanesulfonamide.

¹H-NMP(CDCl₃, δ): 2.88(3H, s), 3.87(3H, s), 6.50(1H, s), 7.02(2H, d, J=8.9 Hz), 7.1–7.4(5H, m), 7.64(1H, d, J=8.0 Hz).

MS(m/z): 277(M⁺), 198.

Preparation Example 62

The procedure of Preparation Example 2 was repeated, except that 208 mg of N-(4'-methoxybiphenyl-2-yl) methanesulfonamide was used in place of 4'-methoxy-2-biphenylacetonitrile, and 1,2-dichloroethane was used in place of methylene chloride. The resulting crude product was purified by TLC (using a 2:1 mixture of hexane and ethyl acetate as the developing solvent) to obtain 178 mg of N-(4'-hydroxy-biphenyl-2-yl)methanesulfonamide.

¹H-NMR(DMSO-d₆, δ): 2.67(3H, s), 6.82(2H, d, J=8.5 Hz), 7.2–7.4 (6H, m), 8.74(1H, s), 9.48(1H, s).

MS(m/z): 263(M⁺), 184.

Preparation Example 63

The procedure of Preparation Example 8 was repeated, except that 601 mg of 4'-methoxybiphenyl-4-ol was used in place of 4-[N-(4-benzyloxybenzyl)amino]phenol. The resulting mixture was stirred at room-temperature for 19 hours. After the reaction mixture was poured into dilute hydrochloric acid, the precipitated crystals were separated by filtration to obtain 783 mg of a crude product of 4'-methoxybiphenyl-4-yl methanesulfonate.

The procedure of Preparation Example 2 was repeated, except that 500 mg of the crude product of 4'-methoxybiphenyl-4-yl methanesulfonate was used in place of 4'-methoxy-2-biphenylacetonitrile. The resulting crude product was purified by TLC (using a 8:1 mixture of chloroform and tetrahydrofuran as the developing solvent) to obtain 250 mg of 4'-hydroxybiphenyl-4-yl methane-sulfonate.

¹H-NMR(DMSO-d₆, δ): 3.37(3H, s), 6.85(2H, d, J=8.6 Hz), 7.37(2H, d, J=8.6 Hz), 7.49(2H, d, J=8.6 Hz), 7.66(2H, d, J=8.6 Hz), 9.56(1H, s).

MS(m/z): 264(M⁺), 185.

Preparation Example 64

The procedure of Preparation Example 2 was repeated, except that 224 mg of (2Z)-2,3-bis(4-methoxyphenyl)prop-2-enenitrile was used in place of 4'-methoxy-2-biphenylacetonitrile, and 1,2-dichloroethane was used in place of methylene chloride. The resulting crude product was purified by TLC (using a 3:1 mixture of chloroform and acetone as the developing solvent) to obtain 130 mg of (2Z)-2,3-bis(4-hydroxyphenyl)-prop-2-enenitrile.

¹H-NMR(CD₃OD, δ): 6.87(4H, d, J=8.8 Hz), 7.3–7.6(3H, m), 7.78(2H, d, J=8.8 Hz).

MS(m/z): 237(M⁺).

Preparation Example 65

The procedure of Preparation Example 28 was repeated, except that 1.145 g of 2-chloropyrimidine was used in place of 4-fluorobenzonitrile. The precipitated crystals were separated by filtration to obtain 691 mg of a crude product of 4-[N-(2-pyrimidyl)amino]benzonitrile.

The procedure of Preparation Example 38 was repeated, except that 298 mg of the crude product of 4-[N-(2-pyrimidyl)amino]-benzonitrile was used in place of 4-[N-(3-pyridyl)amino]benzonitrile, and 390 mg of 4-(tert-butyldimethylsilyloxy)benzyl chloride was used in place of 4-benzyloxybenzyl chloride. The resulting crude product was purified by TLC (using a 1:1 mixture of ethyl acetate and hexane as the developing solvent) to obtain 228 mg of 4-[N-(4-tert-butyldimethylsilyl-oxybenzyl)-N-(2-pyrimidyl)amino]benzonitrile.

¹H-NMR(CDCl₃, δ): 0.20(6H, s), 0.99(9H, s), 4.94(2H, s), 6.86(2H, d, J=8.0 Hz), 7.04(2H, d, J=8.0 Hz), 7.32(2H, d, J=8.5 Hz), 7.5–8.0(4H, m), 8.3–8.6(1H, m).

MS(m/z): 416(M⁺), 221, 195.

Preparation Example 66

The procedure of Preparation Example 47 was repeated, except that 211 mg of 4-[N-(4-tert-butyldimethylsilyloxybenzyl)-N-(2-pyrimidyl)amino]benzonitrile was used in place of N-(4-tert-butyl-dimethylsilyloxybenzyl)-N-(4-cyanophenyl)-2-thiophenecarboxamide.

The resulting crude product was purified by TLC (using a 19:1 mixture of chloroform and methanol as the developing solvent) to obtain 89 mg of 4-[N-(4-hydroxybenzyl)-N-(2-pyrimidyl)amino]benzonitrile.

¹H-NMR(CD₃OD, δ): 5.03(2H, d, J=4.5 Hz), 6.78(2H, d, J=8.3 Hz), 7.06(2H, d, J=8.3 Hz), 7.50(2H, d, J=8.0 Hz), 7.6–8.7(5H, m).

MS(m/z): 302(M⁺), 195, 107.

Preparation Example 67

The procedure of Example 96 was repeated, except that 661 mg of 4-aminobenzyl cyanide was used in place of 4'-aminobiphenyl-4-ol, and 7.5 ml of N,N-dimethylacetamide and 635 mg of sulfamoyl chloride were used. Thus, there was obtained 951 mg of a crude product of amino[4-(cyanomethyl)phenyl]sulfonamide.

¹H-NMR(DMSO-d₆, δ): 3.92(2H, s), 7.08(2H, s), 7.16 (2H, d, J=8.8 Hz), 7.24(2H, d, J=8.8 Hz), 9.52(1H, s).

MS(m/z): 211(M⁺), 131.

Preparation Example 68

A mixture composed of 738 mg of the crude product of amino[4-(cyanomethyl)phenyl]sulfonamide, 0.425 ml of 4-anisaldehyde, 524 mg of potassium carbonate, and 3.5 ml of methanol was heated under reflux for 2 hours. After the reaction mixture was poured into water and acidified with dilute hydrochloric acid, the product was extracted with ethyl acetate. The organic layer was washed with water and dried over anhydrous magnesium sulfate. After the solvent was distilled off, the resulting crude product was purified by silica gel column chromatography (using a 2:1 mixture of chloroform and tetrahydrofuran as the eluent) to obtain 98 mg of (2Z)-2-[4-(sulfamoylamino)-phenyl]-3-(4-methoxyphenyl)prop-2-enenitrile.

¹H-NMR(DMSO-d₆, δ): 3.84(3H, s), 7.10(2H, d, J=8.6 Hz), 7.21(2H, s), 7.25(2H, d, J=8.6 Hz), 7.63(2H, d, J=8.6 Hz), 7.82(1H, s), 7.91(2H, d, J=8.6 Hz), 9.78(1H, s).

MS(m/z): 329(M⁺), 250.

Preparation Example 69

The procedure of Preparation Example 2 was repeated, except that 63 mg of (2Z)-2-[4-(N-sulfamoylamino)phenyl]-3-(4-methoxyphenyl)-prop-2-enenitrile was used in place of 4'-methoxy-2-biphenylacetonitrile, and 1,2-dichloroethane was used in place of methylene chloride. The resulting crude product was purified by TLC (using a 2:1 mixture of chloroform and acetone as the developing solvent) to obtain 17 mg of (2Z)-2-[4-(sulfamoylamino)phenyl]-3-(4-hydroxyphenyl)prop-2-enenitrile.

¹H-NMR(DMSO-d₆, δ): 6.89(2H, d, J=8.8 Hz), 7.19(2H, s), 7.24(2H, d, J=8.8 Hz), 7.60(2H, d, J=9.0 Hz), 7.74(1H, s), 7.81(2H, d, J=9.0 Hz), 9.74(1H, s), 10.14(1H, s).

MS(m/z): 315(M⁺), 236.

Preparation Example 70

The procedure of Preparation Example 2 was repeated, except that 1.465 g of methyl 4-[(1Z)-2-cyano-2-(4-methoxyphenyl)vinyl]phenyl-carboxylate was used in place of 4'-methoxy-2-biphenylacetonitrile, and 1,2-dichloroethane was used in place of methylene chloride. The resulting crude product was purified by TLC (using a 10:1 mixture of chloroform and tetrahydrofuran as the developing solvent) to obtain 524 mg of methyl 4-[(1Z)-2-cyano-2-(4-hydroxyphenyl)vinyl]phenylcarboxylate.

¹H-NMR(DMSO-d₆, δ): 3.89(3H, s), 6.90(2H, d, J=8.7 Hz), 7.63(2H, d, J=8.7 Hz), 7.92(1H, s), 8.00(2H, d, J=8.4 Hz), 8.06(2H, d, J=8.4 Hz), 10.00(1H, s).

MS(m/z 279(M⁺), 248, 220.

| Tablets: | |
|---|---|
| | mg/tablet |
| Active ingredient | 5.0 |
| Starch | 10.0 |
| Lactose | 73.0 |
| Carboxymethyl cellulose calcium salt | 10.0 |
| Talc | 1.0 |
| Magnesium stearate | 1.0 |
| | 100.0 |

The active ingredient is pulverized to a particle size of 70 microns or less. Then, starch, lactose and carboxymethyl cellulose calcium salt are added thereto and thoroughly mixed therewith. After the addition of 10% starch paste, the above powder mixture is agitated and blended to prepare granules. After drying, these granules are adjusted to a particle diameter of about 1,000 microns, and mixed with talc and magnesium stearate. The resulting mixture is formed into tablets.

What is claimed is:

1. A compound of Formula [I] or its pharmaceutically acceptable salts:

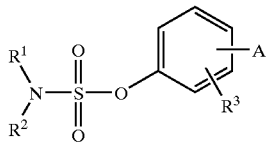

wherein:
- $R^1$ and $R^2$ each independently represent a hydrogen atom;
- $R^3$ represents a hydrogen atom, a halogen atom, a lower alkyl group, $-OSO_2NR^1R^2$, a lower alkanoylamino group, a nitro group or a cyano group; and
- A represents a group represented by the following formula:

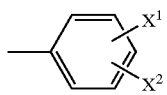

where $X^1$ and $X^2$ each independently represent a hydrogen atom, a halogen atom, a halogen-substituted lower alkyl group, a cyano-substituted lower alkyl group, a lower alkoxy group, a lower alkanoyloxy group, an organic sulfonyloxy group, an amino group, a lower alkanoylamino group, $-NHSO_2NR^1R^2$, an organic sulfonylamino group, a nitro group, a cyano group, a carboxyl group or a lower alkoxycarbonyl group, or a naphthyl group; provided that, when $R^3$ represents a hydrogen atom, either $X^1$ or $X^2$ represents a group which is not a hydrogen atom.

2. A compound of Formula [I] or its pharmaceutically acceptable salts as claimed in claim 1 wherein $R^3$ represents a hydrogen atom or a halogen atom.

3. A compound of Formula [I] or its pharmaceutically acceptable salts as claimed in claim 1 wherein A is located at the 4-position.

4. A compound of Formula [I] or its pharmaceutically acceptable salts as claimed in claim 1 wherein A represents a group represented by the following formula:

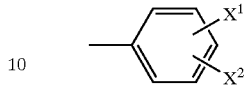

where $X^1$ and $X^2$ each independently represent a hydrogen atom, a halogen atom, a halogen-substituted lower alkyl group, a cyano-substituted lower alkyl group, a lower alkoxy group, a lower alkanoyloxy group, an organic sulfonyloxy group, an amino group, a lower alkanoylamino group, $-NHSO_2NR^1R^2$, an organic sulfonylamino group, a nitro group, a cyano group, a carboxyl group or a lower alkoxycarbonyl group.

5. A compound of Formula [I] or its pharmaceutically acceptable salts as claimed in claim 3 wherein $X^1$ and $X^2$ are each located at the 2- or 4-position of the phenyl group.

6. A steroid sulfatase inhibitor containing a steroid sulfatase-inhibiting amount of a compound of Formula [I] or its pharmaceutically acceptable salt as claimed in claim 1.

7. A pharmaceutical composition comprising a pharmaceutically effective amount of a compound of Formula [I] or its pharmaceutically acceptable salt as claimed in claim 1, and a pharmaceutically acceptable adjuvant.

8. A method for the treatment of breast cancer, which comprises administering a pharmaceutically effective amount of a compound of Formula [I] or it pharmaceutically acceptable salt as claimed in claim 1, to a human being in need thereof.

* * * * *